US007473424B2

(12) United States Patent
Burton et al.

(10) Patent No.: US 7,473,424 B2
(45) Date of Patent: Jan. 6, 2009

(54) ANTI-DENGUE VIRUS ANTIBODIES AND COMPOSITIONS

(75) Inventors: Dennis R. Burton, La Jolla, CA (US); Paul W. H. I. Parren, Odijk (NL); Sidney Yee, Singapore (SG)

(73) Assignee: The Scripps Research Institute, La Jolla, CA (US)

( * ) Notice: Subject to any disclaimer, the term of this patent is extended or adjusted under 35 U.S.C. 154(b) by 330 days.

(21) Appl. No.: 10/756,125

(22) Filed: Jan. 12, 2004

(65) Prior Publication Data
US 2004/0209244 A1 Oct. 21, 2004

Related U.S. Application Data

(60) Provisional application No. 60/443,924, filed on Jan. 31, 2003.

(51) Int. Cl.
*A61K 39/42* (2006.01)
*A61K 39/12* (2006.01)
(52) U.S. Cl. .................... 424/159.1; 424/218.1
(58) Field of Classification Search .............. 424/159.1, 424/218.1
See application file for complete search history.

(56) References Cited
U.S. PATENT DOCUMENTS
6,870,032 B1 * 3/2005 Flamand et al. .......... 530/388.3

FOREIGN PATENT DOCUMENTS
FR  WO 00/75665 A1 * 12/2000

OTHER PUBLICATIONS

Valdés et al. Human Dengue Antibodies against Structural and Nonstructural proteins, Clinical and Diagnostic Laboratory Immunology, 2000, 7(5):856-857.*
Peng et al. Dengue Bulletin, 2004, 28:168-173.*
Shresta et al. J. Virology, 2006, 80(20):10208-10217.*
Seema and S. K. Jain, Indian Journal of Clin. Biochem., 2005, 20(2):92-103.*
Burke et al., 38(1) Am. J. Trop. Med. Hyg. 172-180 (1988).
Graham et al., 61(3) Am. J. Trop. Med. Hyg. 412-419 (1999).
Guzman et al., 11(4) Rev Panam Salud Publica 223-227 (2002).
Guzman et al., 355 Lancet 1902-1903 (2000).
Halstead et al., 75 Am. J. Hyg. 202-211 (1962).
Halstead et al., 8(12) Emerg. Infect. Dis. 1474-1479 (2002).
Halstead et al., 128(1) J. Infect. Dis. 15-22 (1973).
Halstead et al., 132(3) J. Immunol. 1529-1532 (1984).
Halstead et al., 31(1) Infect. Immun. 102-106 (1981).
Halstead et al., 42(5) Yale J. Biol. Med. 311-328 (1970).
Halstead, 140(4) J. Infect. Dis. 527-533 (1979).
Halstead, 31 Prog. Allergy 301-364 (1982).
Innis et al., 40(4) Am. J. Trop. Med. Hyg. 418-427 (1989).
Kliks et al., 38(2) Am. J. Trop. Med. Hyg. 411-419 (1988).
Kliks et al., 40(4) Am. J. Trop. Med Hyg. 444-451 (1989).
Kochel et al., 360 Lancet 310-312 (2002).
Morens et al., 22 J. Med. Virol. 169-174 (1987).
Morens et al., 71 J. Gen. Virol. 2909-2914 (1990).
Myers et al., 59(8) Indian J. Med. Res. 1231-1236 (1971).
Rico-Hesse, 174(2) Virology 479-493 (1990).
Sabin, 1 Am. J. Trop. Med. Hyg. 30-50 (1952).
Sangkawibha et al., 120(5) Am. J. Epidemiol. 653-669 (1984).
Vaughn et al., 181 J. Infect. Dis. 2-9 (2000).
Wang et al., 74(7) J. Virol. 3227-3234 (2000).
Watts et al., 354 Lancet 1431-1434 (1999).
Winter et al., 17(4) Am. J. Trop. Med. Hyg. 590-599 (1968).

* cited by examiner

*Primary Examiner*—Stacy B Chen
(74) *Attorney, Agent, or Firm*—Hugh Wang; Thomas Fitting

(57) ABSTRACT

The present invention relates to at least one novel anti-Dengue virus antibody, including isolated nucleic acids that encode at least one anti-Dengue virus antibody, vectors, host cells, transgenic animals or plants, and methods of making and using thereof, including therapeutic compositions, methods and devices.

5 Claims, 8 Drawing Sheets

Panel A

Titration of Dengue Antigen
Against 25 μg/mL of Antibody

Panel B

Panel C

Figure 2
Sequence ID No: 1

```
        10        20        30        40        50        60        70        80        90       100
GCCGCCACCATGGAATGGAGCTGGGTCTTTCTCTTCTTCCTGTCAGTAACTACAGGTGTCCACTCCCAGGTTCAGCTGGTTCAGTCTGGGGCTGAGGTGA
       110       120       130       140       150       160       170       180       190       200
AGAAGCCTGGGGCCTCAGTGAAGGTTTCCTGCAAGGCATCTGGATACACTTTCACCAACTACTTTCTGCACTGGGTGCGACAGGCCCCCGGACAAGGGCT
       210       220       230       240       250       260       270       280       290       300
TGAGTGGATGGGAATTATCAAGCCTAGTAGTGGTGGTACAACCAACGCACAGAAGTTCCAGGGCAGAGTCACCATGACCAGGGACACGTCCACGAACACT
       310       320       330       340       350       360       370       380       390       400
TTCTACATGGAGCTGAGCAGCCTGATATCTGAGGACACGGCCGTGTATTACTGTGCGCGAGAATCCACTCCCATATCAGTGGCCGACGACTACTACTTCG
       410       420       430       440
GTATGGACGTCTGGGGCCAAGGGACCACGGTCACCGTGAGCTCA
```

Figure 3
Sequence ID No: 2

```
         10        20        30        40        50        60        70        80        90       100
AAGCTTACCATGGGTGTGCCCACTCAGGTCCTGGGGTTGCTGCTGCTGTGGCTTACAGATGCCAGATGTCAGTCCGTGCTGACTCAGCCACCCTCAGCGT
        110       120       130       140       150       160       170       180       190       200
CTGGGACCCCCGGGCAGAGGGTCACCATCTCTTGTTCTGGAAGCACCTCCAACATCGGAAGTAATACTGTAAACTGGTACCAGCAGCTCCCAGGAACGGC
        210       220       230       240       250       260       270       280       290       300
CCCCAAACTCCTCATCTATAGTAATGATCAGCGGCCCTCAGGGGTCCCTGACCGATTCTCTGGCTCCAAGTCTGGCACCTCAGCCTCCCTGGCCATCAGT
        310       320       330       340       350       360       370       380       390       400
GGGCTCCAGTCTGAGGATGAGGCTGATTATTACTGTGCAGCATGGGATGACAGCCTGAATGGCCTATTCGGCGGAGGGACCAAGCTGACCGTCCTAGGTC
        410       420       430       440       450       460       470       480       490       500
AGCCCAAGGCTGCCCCCTCGGTCACTCTGTTCCCGCCCTCCTCTGAGGAGCTTCAAGCCAACAAGGCCACACTGGTGTGTCTCATAAGTGACTTCTACCC
        510       520       530       540       550       560       570       580       590       600
GGGAGCCGTGACAGTGGCCTGGAAGGCACATAGCAGCCCCGTCAAGGCGGGAGTGGAGACCACCACACCCTCCAAACAAAGCAACAACAAGTACGCGGCC
        610       620       630       640       650       660       670       680       690       700
AGCAGCTACCTGAGCCTGACGCCTGAGCAGTGGAAGTCCCACAGAAGCTACAGCTGCCAGGTCACGCATGAAGGGAGCACCGTGGAGAAGACAGTGCGCCC
        710
CTACAGAATGTTCATAA
```

Figure 4
Sequence ID No: 3

Dengue mAb – Heavy Chain

```
         10        20        30        40        50        60        70        80        90       100
AATMEWSWVFLFFLSVTTGVHSQVQLVQSGAEVKKPGASVKVSCKASGYTFTNYFLHWVRQAPGQGLEWMGIIKPSSGGTTNAQKFQGRVTMTRDTSTNT
        110       120       130       140
FYMELSSLISEDTAVYYCARESTPISVADDYYFGMDVWGQGTTVTVSS
```

| CLONE | FR1 | CDR1 | FR2 | CDR2 |
|-------|-----|------|-----|------|
| DEN3 | SGAEVKKPGASVKVSCKASGYTF | TNYFLH | WVRQAPGQGLEWMG | IIKPSSGGTTNAQKFQG |

| CLONE | FR3 | CDR3 | FR4 |
|-------|-----|------|-----|
| DEN3 | RVTMTRDTSTNTFYMELSSLISEDTAVYYCAR | ESTPISVADDYYFGMDV | WGQGTTVTVSS |

Figure 5
Sequence ID No: 4

Dengue mAb – Light Chain

```
        10        20        30        40        50        60        70        80        90       100
KLTMGVPTQVLGLLLLWLTDARCQSVLTQPPSASGTPGQRVTISCSGSTSNIGSNTVNWYQQLPGTAPKLLIYSNDQRPSGVPDRFSGSKSGTSASLAIS
       110       120       130       140       150       160       170       180       190       200
GLQSEDEADYYCAAWDDSLNGLFGGGTKLTVLGQPKAAPSVTLFPPSSEELQANKATLVCLISDFYPGAVTVAWKADSSPVKAGVETTTPSKQSNNKYAA
       210       220       230
SSYLSLTPEQWKSHRSYSCQVTHEGSTVEKTVAPTECS *
```

| CLONE | FR1 | CDR1 | FR2 | CDR2 |
|-------|-----|------|-----|------|
| DEN3 | LTQPPSASGTPGQRVTISC | SGSTSNIGSNTVN | WYQQLPGTAPKLLIY | SNDQRPS |

| CLONE | FR3 | CDR3 | FR4 |
|-------|-----|------|-----|
| DEN3 | GVPDRFSGSKSGTSASLAISGLQSEDEADYYC | AAWDDSLNGL | FGGGTKL |

SEQUENCE LISTING

```
<160> NUMBER OF SEQ ID NOS: 4

<210> SEQ ID NO 1
<211> LENGTH: 444
<212> TYPE: DNA
<213> ORGANISM: Artificial
<220> FEATURE:
<223> OTHER INFORMATION: heavy chain

<400> SEQUENCE: 1
gccgccacca tggaatggag ctgggtcttt ctcttcttcc tgtcagtaac tacaggtgtc      60
cactcccagg ttcagctggt tcagtctggg gctgaggtga agaagcctgg ggcctcagtg     120
aaggtttcct gcaaggcatc tggatacact ttcaccaact actttctgca ctgggtgcga     180
caggcccccg gacaagggct tgagtggatg ggaattatca agcctagtag tggtggtaca     240
accaacgcac agaagttcca gggcagagtc accatgacca gggacacgtc cacgaacact     300
ttctacatgg agctgagcag cctgatatct gaggacacgg ccgtgtatta ctgtgcgcga     360
gaatccactc ccatatcagt ggccgacgac tactacttcg gtatggacgt ctggggccaa     420
gggaccacgg tcaccgtgag ctca                                            444

<210> SEQ ID NO 2
<211> LENGTH: 718
<212> TYPE: DNA
<213> ORGANISM: Artificial
<220> FEATURE:
<223> OTHER INFORMATION: light chain

<400> SEQUENCE: 2
aagcttacca tgggtgtgcc cactcaggtc ctggggttgc tgctgctgtg gcttacagat      60
gccagatgtc agtccgtgct gactcagcca ccctcagcgt ctgggacccc cgggcagagg     120
gtcaccatct cttgttctgg aagcacctcc aacatcggaa gtaatactgt aaactggtac     180
cagcagctcc caggaacggc ccccaaactc ctcatctata gtaatgatca gcggccctca     240
ggggtccctg accgattctc tggctccaag tctggcacct cagcctccct ggccatcagt     300
gggctccagt ctgaggatga ggctgattat tactgtgcag catgggatga cagcctgaat     360
ggcctattcg gcggagggac caagctgacc gtcctaggtc agcccaaggc tgccccctcg     420
gtcactctgt tcccgccctc ctctgaggag cttcaagcca acaaggccac actggtgtgt     480
```

```
ctcataagtg acttctaccc gggagccgtg acagtggcct ggaaggcaca tagcagcccc    540
gtcaaggcgg gagtggagac caccacaccc tccaaacaaa gcaacaacaa gtacgcggcc    600
agcagctacc tgagcctgac gcctgagcag tggaagtccc acagaagcta cagctgccag    660
gtcacgcatg aagggagcac cgtggagaag acagtgcgcc cctacagaat gttcataa     718
```

```
<210> SEQ ID NO 3
<211> LENGTH: 148
<212> TYPE: PRT
<213> ORGANISM: Artificial
<220> FEATURE:
<223> OTHER INFORMATION: heavy chain

<400> SEQUENCE: 3

Ala Ala Thr Met Glu Trp Ser Trp Val Phe Leu Phe Phe Leu Ser Val
1               5                   10                  15

Thr Thr Gly Val His Ser Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Asn Tyr Phe Leu His Trp Val Arg Gln Ala Pro Gly
    50                  55                  60

Gln Gly Leu Glu Trp Met Gly Ile Ile Lys Pro Ser Ser Gly Gly Thr
65                  70                  75                  80

Thr Asn Ala Gln Lys Phe Gln Gly Arg Val Thr Met Thr Arg Asp Thr
                85                  90                  95

Ser Thr Asn Thr Phe Tyr Met Glu Leu Ser Ser Leu Ile Ser Glu Asp
            100                 105                 110

Thr Ala Val Tyr Tyr Cys Ala Arg Glu Ser Thr Pro Ile Ser Val Ala
        115                 120                 125

Asp Asp Tyr Tyr Phe Gly Met Asp Val Trp Gly Gln Gly Thr Thr Val
    130                 135                 140

Thr Val Ser Ser
145

<210> SEQ ID NO 4
<211> LENGTH: 238
<212> TYPE: PRT
<213> ORGANISM: Artificial
<220> FEATURE:
<223> OTHER INFORMATION: light chain

<400> SEQUENCE: 4

Lys Leu Thr Met Gly Val Pro Thr Gln Val Leu Gly Leu Leu Leu Leu
1               5                   10                  15

Trp Leu Thr Asp Ala Arg Cys Gln Ser Val Leu Thr Gln Pro Pro Ser
            20                  25                  30

Ala Ser Gly Thr Pro Gly Gln Arg Val Thr Ile Ser Cys Ser Gly Ser
        35                  40                  45

Thr Ser Asn Ile Gly Ser Asn Thr Val Asn Trp Tyr Gln Gln Leu Pro
    50                  55                  60

Gly Thr Ala Pro Lys Leu Leu Ile Tyr Ser Asn Asp Gln Arg Pro Ser
65                  70                  75                  80

Gly Val Pro Asp Arg Phe Ser Gly Ser Lys Ser Gly Thr Ser Ala Ser
                85                  90                  95

Leu Ala Ile Ser Gly Leu Gln Ser Glu Asp Glu Ala Asp Tyr Tyr Cys
            100                 105                 110
```

-continued

```
Ala Ala Trp Asp Asp Ser Leu Asn Gly Leu Phe Gly Gly Gly Thr Lys
        115                 120                 125

Leu Thr Val Leu Gly Gln Pro Lys Ala Ala Pro Ser Val Thr Leu Phe
    130                 135                 140

Pro Pro Ser Ser Glu Glu Leu Gln Ala Asn Lys Ala Thr Leu Val Cys
145                 150                 155                 160

Leu Ile Ser Asp Phe Tyr Pro Gly Ala Val Thr Val Ala Trp Lys Ala
                165                 170                 175

Asp Ser Ser Pro Val Lys Ala Gly Val Glu Thr Thr Thr Pro Ser Lys
            180                 185                 190

Gln Ser Asn Asn Lys Tyr Ala Ala Ser Ser Tyr Leu Ser Leu Thr Pro
        195                 200                 205

Glu Gln Trp Lys Ser His Arg Ser Tyr Ser Cys Gln Val Thr His Glu
    210                 215                 220

Gly Ser Thr Val Glu Lys Thr Val Ala Pro Thr Glu Cys Ser
225                 230                 235
```

ANTI-DENGUE VIRUS ANTIBODIES AND COMPOSITIONS

RELATED APPLICATIONS

This application claims priority under 35 U.S.C. 119(e) from Provisional Application Ser. No. 60/443,924 filed on 31 Jan. 2003, the entirety of which is incorporated by reference herein.

BACKGROUND OF THE INVENTION

The present invention relates to antibodies, including specified portions or variants, specific for at least one Dengue virus NS protein or fragment thereof, as well as nucleic acids encoding such anti-Dengue virus antibodies, complementary nucleic acids, vectors, host cells, and methods of making and using thereof, including therapeutic formulations, administration and devices.

Dengue Shock Syndrome (DSS) and dengue hemorrhagic fever (DHF) are caused by one of four closely related, but antigenically distinct, virus serotypes (DEN-1, DEN-2, DEN-3, and DEN-4), of the genus *Flavivirus*. Infection with one of these serotypes does not provide cross-protective immunity, so persons living in a dengue-endemic area can have at least four dengue infections during their lifetimes. Dengue is primarily a disease of the tropics, and the viruses that cause it are maintained in a cycle that involves humans and *Aedes aegypti*, a domestic, day-biting mosquito that prefers to feed on humans. Infection with dengue viruses produces a spectrum of clinical illness ranging from a nonspecific viral syndrome to severe and fatal hemorrhagic disease. Important risk factors for DHF include the strain and serotype of the infecting virus, as well as the age, immune status, and genetic predisposition of the patient.

Dengue may be the most important mosquito-borne viral disease-affecting humans; its global distribution is comparable to that of malaria, and an estimated 2.5 billion people live in areas at risk for epidemic transmission. Each year, tens of millions of cases of dengue fever occur and, depending on the year, up to hundreds of thousands of cases of DHF. The case-fatality rate of DHF in most countries is about 5%; most fatal cases are among children and young adults.

Accordingly, there is a need to provide new therapeutic, prophylactic and diagnostic agents against Dengue virus. Anti-Dengue virus antibodies or fragments of the present invention provide new therapeutic and/or prophylactic agents to treat and/or prevent Dengue virus infection and its associated diseases. The anti-Dengue virus antibodies and fragments of the present invention also provide diagnostic reagents for detecting infection or epidemiological investigation in the population.

SUMMARY OF THE INVENTION

The present invention provides isolated human, primate, rodent, mammalian, chimeric, humanized and/or CDR-grafted anti-Dengue virus antibodies, immunoglobulins, cleavage products and other specified portions and variants thereof, as well as anti-Dengue virus antibody compositions, encoding or complementary nucleic acids, vectors, host cells, compositions, formulations, devices, transgenic animals, transgenic plants, and methods of making and using thereof, as described and enabled herein, and in combination with what is known in the art.

The present invention also provides at least one isolated anti-Dengue virus antibody as described herein. An antibody according to the present invention includes any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, that can be incorporated into an antibody of the present invention. An antibody of the invention can include or be derived from any mammal, such as, but not limited to, a human, a mouse, a rabbit, a rat, a rodent, a primate, or any combination thereof, and the like.

The present invention provides, in one aspect, isolated nucleic acid molecules comprising, complementary, or hybridizing to, a polynucleotide encoding specific anti-Dengue virus antibodies, comprising at least one specified sequence, domain, portion or variant thereof. The present invention further provides recombinant vectors comprising said anti-Dengue virus antibody nucleic acid molecules, host cells containing such nucleic acids and/or recombinant vectors, as well as methods of making and/or using such antibody nucleic acids, vectors and/or host cells.

At least one antibody of the invention binds at least one specified epitope specific to at least one Dengue virus protein, subunit, fragment, portion or any combination thereof, including, but not limited to, Dengue virus proteins C, preM, E, NS1, NS2A, NS2B, NS3, NS4A, NS4B and NS5. At least one epitope can comprise at least one antibody binding region that comprises at least one portion of said protein, which epitope is preferably comprised of at least 1 to 5 amino acids of at least one portion thereof, such as but not limited to, at least one functional, extracellular, soluble, hydrophilic, external or cytoplasmic domain of said protein, or any portion thereof. At least one antibody of the present invention binds to a Dengue virus NS-1 protein.

At least one antibody can optionally comprise at least one specified portion of at least one complementarity determining region (CDR) (e.g., CDR1, CDR2 or CDR3 of the heavy or light chain variable region) and/or at least one constant or variable framework region or any portion thereof. The at least one antibody amino acid sequence can further optionally comprise at least one specified substitution, insertion or deletion as described herein or as known in the art.

The present invention also provides at least one isolated anti-Dengue virus antibody as described herein, wherein the antibody has at least one activity, such as, but not limited to, inhibition or enhancement of Dengue virus-induced cell death or damage resulting from activity of the host's immune system, neutralization of a biological activity of a Dengue virus NS protein, inhibition of Dengue virus replication, preventing Dengue virus-related disease in a patient, mitigating symptoms of Dengue virus infection in a patient, diagnosing the presence of Dengue virus in a sample, and epidemiological analysis. A(n) anti-Dengue virus antibody can thus be screened for a corresponding activity according to known methods, such as but not limited to, at least one biological activity towards a Dengue virus protein.

The present invention also provides at least one method for expressing at least one anti-Dengue virus antibody, in a host cell, comprising culturing a host cell as described herein under conditions wherein anti-Dengue virus antibody is expressed in detectable and/or recoverable amounts.

The present invention also provides at least one composition comprising: a) an isolated anti-Dengue virus antibody encoding nucleic acid and/or antibody as described herein; and b) a suitable carrier or diluent. The carrier or diluent can optionally be pharmaceutically acceptable, according to known carriers or diluents. The composition can optionally further comprise at least one further compound, protein or composition.

The present invention further provides at least one anti-Dengue virus antibody method or composition, for administering a therapeutically effective amount to modulate or treat at least one Dengue virus related condition in a cell, tissue, organ, animal or patient and/or, prior to, subsequent to, or during a related condition, as known in the art and/or as described herein.

The present invention also provides at least one composition, device and/or method of delivery of a therapeutically or prophylactically effective amount of at least one anti-Dengue virus antibody, according to the present invention.

The present invention further provides at least one anti-Dengue virus antibody method or composition, for diagnosing at least one Dengue virus related condition in a cell, tissue, organ, animal, patient or population of subjects, and/or, prior to, subsequent to, or during a related condition, as known in the art and/or as described herein.

The present invention also provides at least one composition, device and/or method of delivery for diagnosing the presence or absence of at least one anti-Dengue virus antibody in a sample, according to the present invention.

DESCRIPTION OF THE FIGURES

FIG. 1, Panel A shows a titration of Dengue antigen against IgG DEN3 mAb and Fab Sid33. FIG. 1, Panel B shows a titration of Dengue antigen against Sid33 Fab at 20 µl/mL. FIG. 1, Panel C shows a titration of Fab Sid33 and IgG DEN3 antibodies against Dengue antigen at (1:500). Based on data from antigen titration, peak binding occurred at approximately (1:500) dilution of Dengue antigen. Thus, antibodies were titrated against the antigen at (1:500) beginning at 25 µg/mL to create a binding curve.

FIG. 2: Shows DNA sequences of the anti-Dengue virus mAb heavy chain variable regions (SEQ ID NO: 1).

FIG. 3: Shows DNA sequences of the anti-Dengue virus mAb light chain variable regions (SEQ ID NO: 2).

FIG. 4: Shows deduced amino acid sequences of the anti-Dengue virus mAb heavy chain variable regions. The amino acid sequences shown (single letter abbreviations) were deduced from DNA sequence. The amino sequences are shown partitioned into the framework (FR) and complementarity determining region (CDR) domains (SEQ ID NO: 3).

FIG. 5: Shows deduced amino acid sequences of the anti-Dengue virus mAb light chain variable regions. The amino acid sequences shown (single letter abbreviations) were deduced from DNA sequence. The amino sequences are shown partitioned into the framework (FR) and complementarity determining region (CDR) domains (SEQ ID NO: 4).

DESCRIPTION OF THE INVENTION

Figure 1:
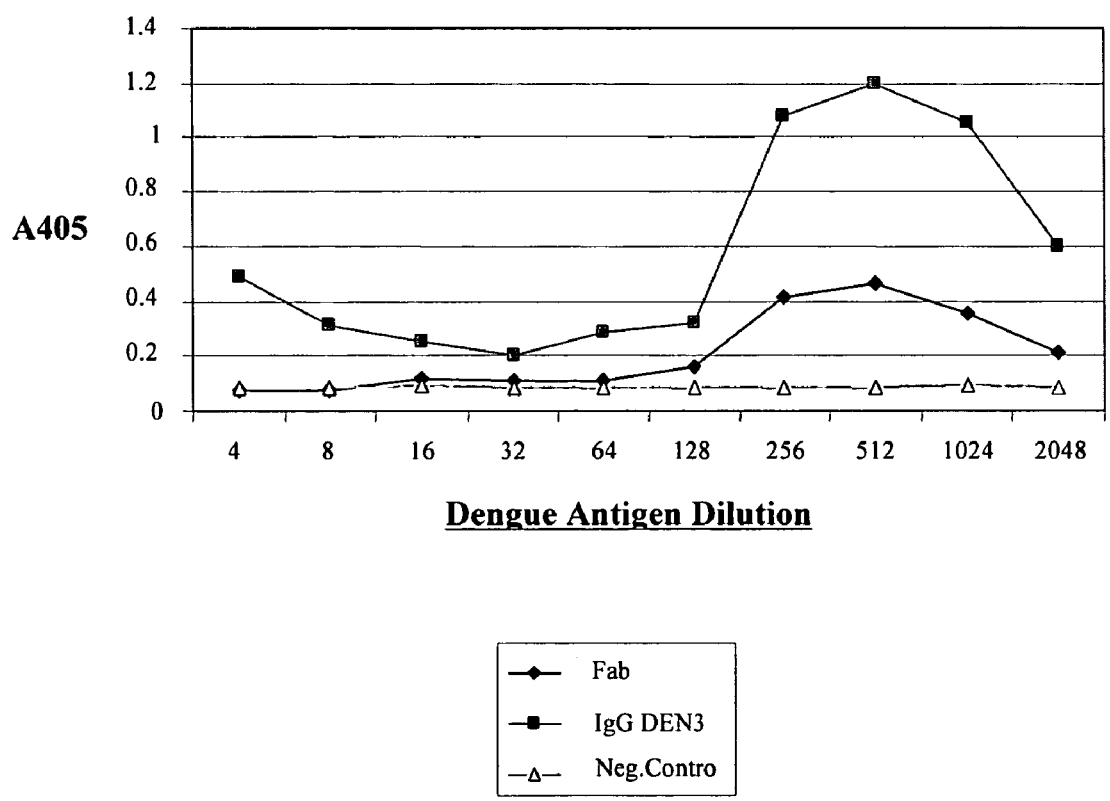
FIG. 1, Panels A, B and C: Shows a graphical representation showing an assay for ability of anti-Dengue virus antibody to inhibit Dengue virus infectivity.
Figure 1:
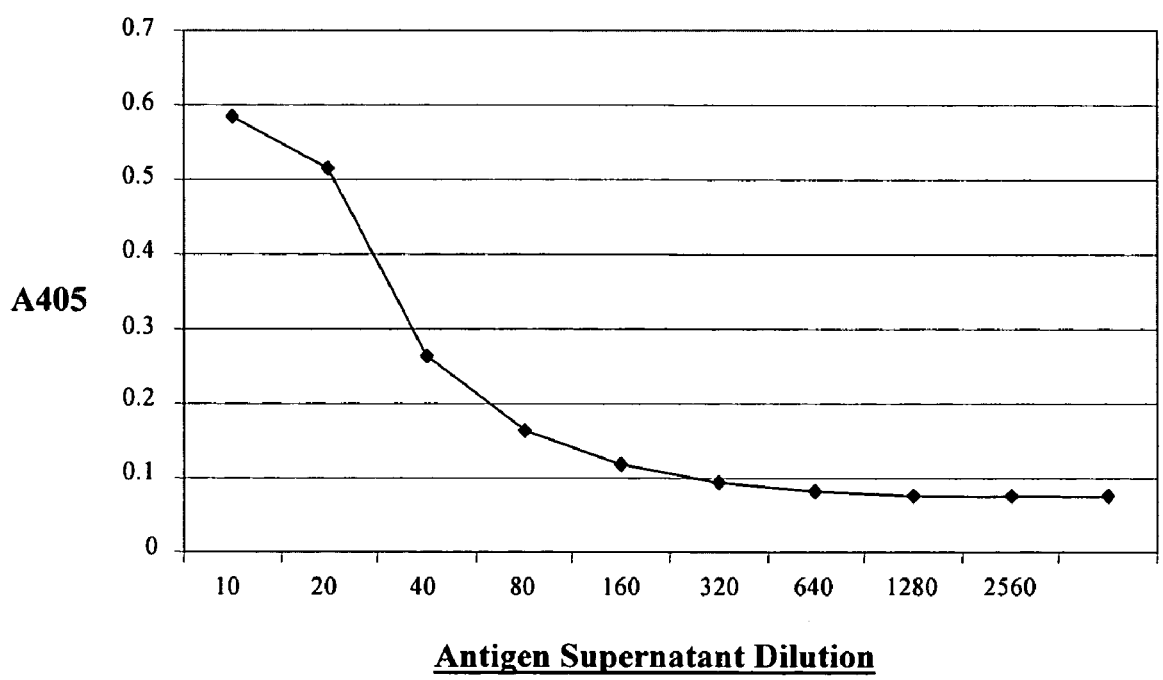
Figure 1:
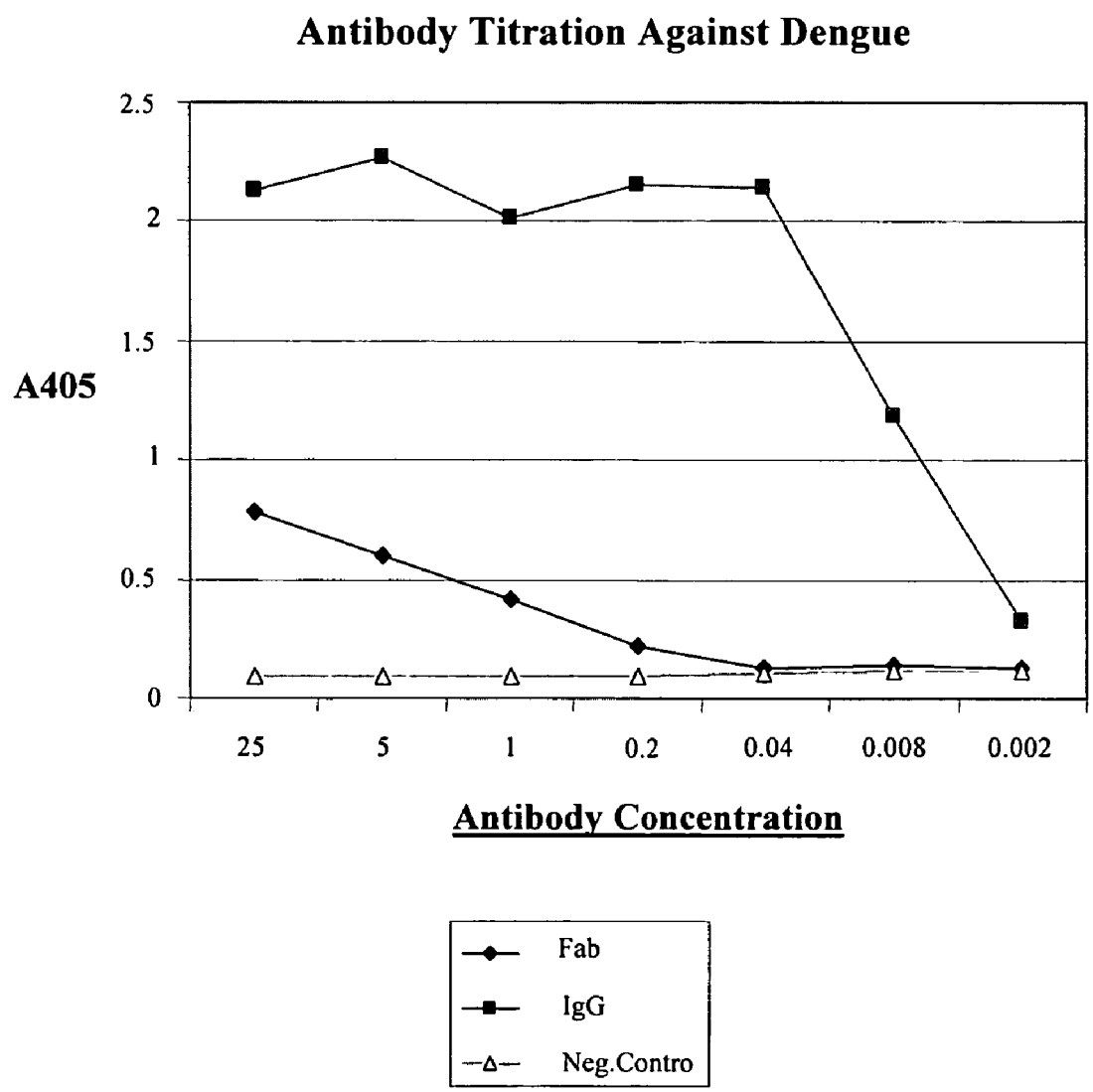
Figure 6:
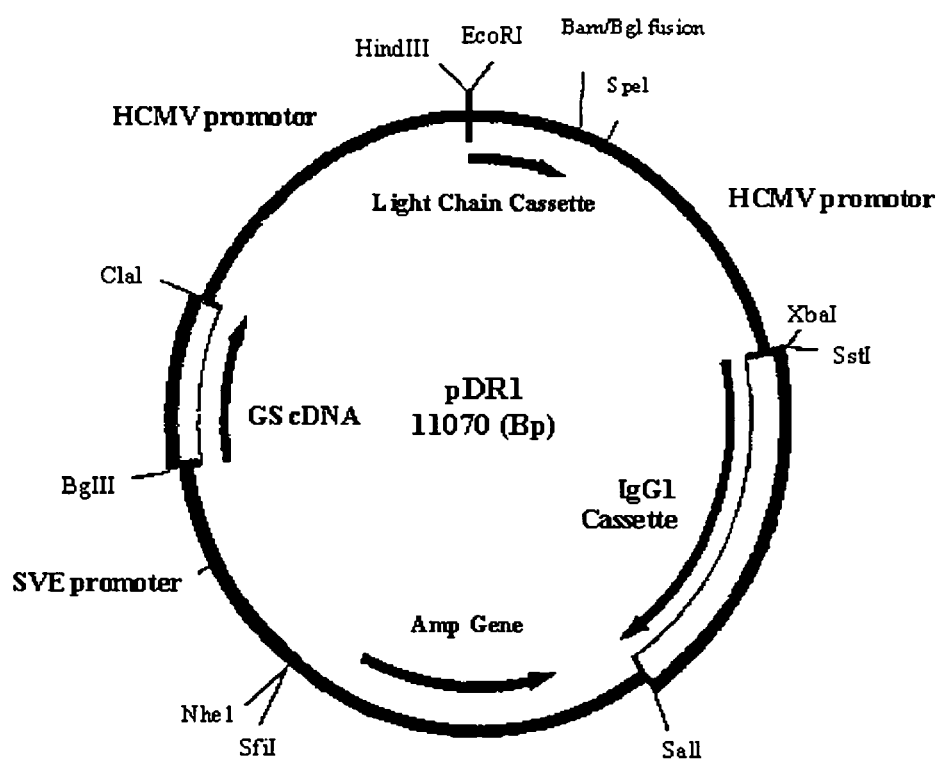
FIG. 6: Shows schematic illustrations of the heavy and light chain expression plasmid pDR1 11070 (bp) used to make the anti-Dengue virus antibody-expressing cells.

The present invention provides isolated, anti-Dengue virus antibodies, as well as compositions and encoding nucleic acid molecules comprising at least one polynucleotide encoding at least one anti-Dengue virus antibody. The present invention further includes, but is not limited to, methods of making and using such nucleic acids and antibodies, including diagnostic and therapeutic compositions, methods and devices.

Dengue viruses are 50 nm spherical enveloped particles with icosahedral capsid symmetry. Virions incorporate a single strand of positive-sense RNA of approximately 11,000 bases. The RNA is packaged within a capsid (C) protein. The surrounding shell is composed of 90 copies of dimeric envelope (E) proteins and interspersed matrix (M) proteins. Fifteen to twenty percent of virion weight is made up of lipids incorporated from host cell membranes; 9 to 10% of virion weight is in glycolipids or glycoproteins.[1]

Dengue viruses belong to the *Flavivirus* genus, some 68 antigenically related viruses whose genes, organized from the 5' end, code for 10 proteins, C, pre-M, E, NS-1 (non-structural), NS2A, NS2B, NS3, NS4A, NS4B, and NS5. Most *flaviviruses* are transmitted between vertebrate hosts by blood-sucking arthropods.

There are four Dengue viruses, Dengue (DEN)-1, -2, -3, and -4. These evolved in sub-human primates from a common ancestor and have been transmitted in an urban cycle, *Aedes aegypti*—humans—*Aedes aegypti*, for around one thousand years.[2]

Dengue viruses share 60+% genome within the Dengue subgroup. Thus, shared antigens are expressed on virion surfaces or the surface of infected cells. Primary infections raise common Dengue antibodies, readily detected by the ELISA and hemagglutination-inhibition tests, but less well detected by plaque reduction neutralization tests (PRNT). PRNT are performed in a wide range of continuous cell lines.[3, 4, 5]

As described by Sabin (1952), adult human volunteers infected with DEN-1 or DEN-2 viruses were protected from clinical illness when challenged with heterologous virus within two months of primary infections. However, viremic infections occurred in mono-immune volunteers challenged with heterologous virus between two and three months after primary infection. These infections "gave rise to malaise and slight fever." Mild illnesses accompanied cross-challenges up to nine months following primary infection and unaltered illnesses thereafter.[6] Other than the studies of Sabin, cross protection among various Dengue viruses and strains has not been studied systematically. Third and fourth Dengue infections are documented in prospective seroepidemiological studies, but seldom result in clinical illness.[7]

The strongest evidence that Dengue antibodies both protect against and enhance Dengue virus infections is the regular occurrence of severe DHF in infants during their first Dengue infection.[8, 9, 10] This group comprises 5% to 10% of all DHF cases and at peak risk period (eight months) infants are four times more likely to develop DHF during a first Dengue infection than are older children during second dengue infections. Initially, infants are completely protected against Dengue illnesses.[11] As maternal antibodies wane below protective threshold (thought to be around 1:10 in a conventional PRNT), infants become at risk to enhanced infections and disease.[9, 12] These infants are susceptible to infection by any Dengue virus type.

This phenomenon has been reproduced experimentally in an in vivo model. Enhanced DEN-2 viremias compared with control animals were observed regularly in five rhesus monkeys infected immediately following intravenous inoculation of small quantities of human cord blood-derived dengue antibodies.[13]

Evidence that DHF/DSS occurs at high frequency during secondary Dengue infections comes from a multitude of sources over more than 40 years of observation. Four prospective studies have documented hospitalized Dengue only among children with pre-hospitalization Dengue antibodies.[14, 15, 16, 17]

Enhanced viremias during secondary DEN-2 infections have been observed in vivo in rhesus monkeys infected in the sequences DEN-1 followed by DEN-2, DEN-3 followed by DEN-2, and DEN-4 followed by DEN-2.[18] Enhanced viremias have not been observed in monkeys infected in other sequences (all nine other sequences have been tried). However, only limited numbers of monkeys were infected in other sequences.

Enhanced viremias, or Antibody-dependent enhancements (ADE), during secondary infections predict (and correlate with) disease severity during secondary dengue infections in children.[19]

ADE can be demonstrated and measured in vitro using as host cells a wide range of primary blood leukocyte and FcR-bearing cell cultures.[20]

Critical site-specific monoclonal antibodies neutralize at low dilutions and enhance at high dilutions. Some group-reactive monoclonal antibodies neutralize at low dilutions and enhance at high dilutions.[20, 21, 22, 23]

Cross-reactive neutralizing antibodies are often observed following a single Dengue virus infection and more often in Dengue-infected Japanese encephalitis immunes.[4,17,24] Despite heterologous antibodies (measured in vitro) second Dengue virus infections occur regularly, only rarely symptomatic. In a 1980 cohort study, inapparent infections were observed in 85% of forty Bangkok school children who experienced secondary DEN-2 infections. Undiluted pre-infection serum from these children prevented DEN-2 infection in cultures of human monocytes. But, undiluted sera from six of the seven cohort children who experienced severe illness did not neutralize DEN-2; ADE was observed.[24] More recently, children acquired clinically overt secondary DEN-3 infections when their pre-illness sera contained heterologous DEN-3 neutralizing antibodies. Use of the autologous DEN-3 strain (virus isolated from patient) significantly reduced neutralizing antibody titers compared with use of laboratory-passaged "standard" strains. The severity of secondary DEN-3 infections was inversely related to the neutralizing antibody titers against autologous DEN-3 strains.

The most dramatic illustration of infection down-regulation by heterotypic antibodies is the non-"virulence" of the American genotype DEN-2. When this virus circulated in Peru in a population partially immune to DEN-1, no DHF was observed.[25] But, the capacity of human anti-DEN-1 sera to neutralize different DEN-2 viruses was not the same: all American genotype DEN-2 viruses were highly neutralized by anti-DEN-1, while anti-DEN-1 poorly neutralized (DHF-producing) SE Asian DEN-2 strains.[26] Asian DEN-2 strains, chronically circulating with other DEN viruses may have been selected to "escape" neutralization by heterotypic antibodies.

A more rapid "escape" phenomenon has been observed. Rapid (month-to-month) disease severity increases were observed during two epidemics in which monotypic DEN-2 was transmitted in humans immune to DEN-1.[27]

Affinity maturation of antibody responses occurs following *flavivirus* infections. This was demonstrated by rising log neutralization indices over a four-year follow-up of American servicemen who were subclinically infected with Japanese Encephalitis Virus. They were bled at one and five years after infection.[28] Affinity maturation offers an explanation of the observation that secondary DEN-2 infections at an interval of twenty years after primary DEN-1 were much more severe than when the same genotype viruses resulted in secondary infections at an interval of four years. This could be the result of antibody becoming more avidly directed at type-specific neutralization site(s) with correspondingly less broad reactivity, permitting ADE to occur.[29]

As used herein, an "Anti-Dengue virus antibody," "Anti-Dengue virus antibody portion," or "Anti-Dengue virus antibody fragment" and/or "Anti-Dengue virus antibody variant" and the like include any protein or peptide containing molecule that comprises at least a portion of an immunoglobulin molecule, such as, but not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of a Dengue virus protein, which can be incorporated into an antibody of the present invention. Such antibody optionally further affects a specific ligand, such as, but not limited to, where such antibody modulates, decreases, increases, antagonizes, angonizes, mitigates, alleviates, blocks, inhibits, abrogates and/or interferes with at least one Dengue virus infectivity activity or replication, or with Dengue virus cellular receptor activity or binding, in vitro, in situ and/or in vivo. As a non-limiting example, a suitable anti-Dengue virus antibody, specified portion or variant of the present invention can bind at least one Dengue virus, or specified portions, variants or domains thereof. A suitable anti-Dengue virus antibody, specified portion, or variant can also optionally affect at least one of Dengue virus activity or function, such as, but not limited to, RNA, DNA or protein synthesis, Dengue virus infectivity, Dengue virus release, Dengue virus receptor signaling, Dengue virus replication, Dengue virus production and/or synthesis and facilitating the destruction or recognition of Dengue virus infected cells by the host immune system. The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian Dengue virus. For example, antibody fragments capable of binding to Dengue virus or portions thereof, including, but not limited to Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and re-aggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the CH, domain and/or hinge region of the heavy chain. The various portions of antibodies can be joined together chemically by conventional techniques, or can be prepared as a contiguous protein using genetic engineering techniques.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations.

Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Bispecific, heterospecific, heteroconjugate or similar antibodies can also be used that are monoclonal, preferably human or humanized, antibodies that have binding specificities for at least two different antigens. In the present case, one of the binding specificities is for at least one Dengue virus protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, 305 NATURE, 537 (1983)). Because of the random assortment of immunoglobulin heavy and light chains, these hybridomas (quadromas) produce a potential mixture of ten different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668; 6,193,967; 6,132,992; 6,106,833; 6,060,285; 6,037,453; 6,010,902; 5,989,530; 5,959,084; 5,959,083; 5,932,448; 5,833,985; 5,821,333; 5,807,706; 5,643,759; 5,601,819; 5,582,996; 5,496,549; 4,676,980; WO 91/00360, WO 92/00373, EP 03089, Traunecker et al., 10 EMBO J., 3655 (1991), Suresh et al., 121 METHODS IN ENZYMOLOGY, 210 (1986), each entirely incorporated herein by reference.

Anti-Dengue virus antibodies (also termed Dengue virus antibodies) useful in the methods and compositions of the present invention can optionally be characterized by high affinity binding to Dengue virus and optionally and preferably having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. (Elliott et al., 344 LANCET, 1125-1127 (1994), entirely incorporated herein by reference).

Utility

The isolated nucleic acids of the present invention can be used for production of at least one anti-Dengue virus antibody or specified variant thereof, which can be used to measure or effect in a cell, tissue, organ or animal (including mammals and humans), to diagnose, monitor, modulate, treat, alleviate, help prevent the incidence of, or reduce the symptoms of, at least one Dengue virus condition, selected from, but not limited to, at least one of an immune disorder or disease, a cardiovascular disorder or disease, an infectious, malignant, and/or neurologic disorder or disease.

Such a method can comprise administering an effective amount of a composition or a pharmaceutical composition comprising at least one anti-Dengue virus antibody to a cell, tissue, organ, animal or patient in need of such modulation, treatment, alleviation, prevention, or reduction in symptoms, effects or mechanisms. The effective amount can comprise an amount of about 0.001 to 50 mg/kg per single (e.g., bolus), multiple or continuous administration, or to achieve a serum concentration of 0.01 to 500 µg/ml serum concentration per single, multiple, or continuous administration, or any effective range or value therein, as done and determined using known methods, as described herein or known in the relevant arts.

Citations

All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel et al. (Ed.), *Current Protocols in Molecular Biology*, (John Wiley & Sons, Inc., New York, N.Y. (1987-1991)); Sambrook et al., *Molecular Cloning: A Laboratory Manual $2^{nd}$ Edition*, (Cold Spring Harbor, N.Y. (1989)); Harlow and Lane, *Antibodies, A Laboratory Manual*, (Cold Spring Harbor, N.Y. (1989)); Colligan et al. (Eds.), *Current Protocols in Immunology*, (John Wiley & Sons, Inc., NY (1994-2001)); Colligan et al., *Current Protocols in Protein Science*, (John Wiley & Sons, NY, N.Y., (1997-2001)).

Antibodies of the Present Invention

At least one anti-Dengue virus antibody of the present invention can be optionally produced by a cell line, a mixed cell line, an immortalized cell or clonal population of immortalized cells, as well known in the art. See, e.g., Ausubel et al. (Ed.), *Current Protocols in Molecular Biology*, (John Wiley & Sons, Inc., New York, N.Y. (1987-2001)); Sambrook et al., *Molecular Cloning: A Laboratory Manual, $2^{nd}$ Edition*, (Cold Spring Harbor, N.Y. (1989)); Harlow and Lane, *Antibodies, A Laboratory Manual*, (Cold Spring Harbor, N.Y. (1989)); Colligan, et al. (Eds.), *Current Protocols in Immunology*, (John Wiley & Sons, Inc., NY (1994-2001)); Colligan et al., *Current Protocols in Protein Science*, (John Wiley & Sons, NY, N.Y., (1997-2001)), each entirely incorporated herein by reference.

Human antibodies that are specific for Dengue virus proteins or fragments thereof can be raised against an appropriate immunogenic antigen, such as isolated Dengue virus protein or a portion thereof (including synthetic molecules, such as synthetic peptides). Other specific or general mammalian antibodies can be similarly raised. Preparation of immunogenic antigens, and monoclonal antibody production can be performed using any suitable technique.

In one approach, a hybridoma is produced by fusing a suitable immortal cell line (e.g., a myeloma cell line) such as, but not limited to, Sp2/0, Sp2/0-AG14, P3/NS1/Ag4-1, P3×63Ag8.653, MCP-11, S-194, or the like, or heteromyelomas, fusion products thereof, or any cell or fusion cell derived therefrom, or any other suitable cell line as known in the art, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, Chapter 2, entirely incorporated herein by reference.

Antibody producing cells can also be obtained from the peripheral blood or, preferably the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; BioInvent, Lund, Sweden; Dyax Corp., Enzon, Affymax/Biosite; Xoma, Berkeley, Calif.; Ixsys. See, e.g., EP 368,684; PCT/GB91/01134; PCT/GB92/01755; PCT/GB92/002240; PCT/GB92/00883; PCT/GB93/00605; U.S. Ser. No. 08/350, 260 (May 12, 1994); PCT/GB94/01422; PCT/GB94/02662; PCT/GB97/01835; (CAT/MRC); WO 90/14443; WO 90/14424; WO 90/14430; PCT/US94/1234; WO 92/18619; WO 96/07754 (Scripps); EP 614989 (MorphoSys); WO 95/16027 (BioInvent); WO 88/06630; WO 90/3809 (Dyax); U.S. Pat. No. 4,704,692 (Enzon); PCT/US91/02989 (Affymax); WO 89/06283; EP 371998; EP 550400; (Xoma); EP 229046; PCT/US91/07149 (Ixsys); or stochastically generated peptides or proteins—U.S. Pat. Nos. 5,723,323; 5,763, 192; 5,814,476; 5,817,483; 5,824,514; 5,976,862; WO 86/05803; EP 590689 (Ixsys, now known as Applied Molecular Evolution (AME), each entirely incorporated herein by reference) or that rely upon immunization of transgenic animals (e.g., SCID mice, Nguyen et al., 41 MICROBIOL. IMMUNOL., 901-907 (1997); Sandhu et al., 16 CRIT. REV. BIOTECHNOL., 95-118 (1996); Eren et al., 93 IMMUNOL., 154-161 (1998), each entirely incorporated by reference as well as related patents and applications) that are capable of producing a repertoire of human antibodies, as known in the art and/or as described herein. Such techniques, include, but are not limited to, ribosome display (Hanes et al., 94 PROC. NATL. ACAD. SCI. USA, 4937-4942 (May, 1997); Hanes et al., 95 PROC. NATL. ACAD. SCI. USA, 14130-14135 (November, 1998); single cell antibody producing technologies (e.g., selected lymphocyte antibody method ("SLAM") (U.S. Pat. No. 5,627,052; Wen et al., 17 J. IMMUNOL., 887-892 (1987); Babcook et al., 93 PROC. NATL. ACAD. SCI. USA, 7843-7848 (1996); gel microdroplet and flow cytometry (Powell et al., 8 BIOTECHNOL., 333-337 (1990); One Cell Systems, Cambridge, Mass.; Gray et al., 182 J. IMM. METH., 155-163 (1995); Kenny et al., 13 BIO/TECHNOL., 787-790 (1995); B-cell selection (Steenbakkers et al., 19 MOLEC. BIOL. REPORTS, 125-134 (1994); Jonak et al., *Progress Biotech Vol. 5 In Vitro Immunization in Hybridoma Technology*, (Borrebaeck (Ed.), Elsevier Science Publishers B. V., Amsterdam, Netherlands (1988)).

Methods for engineering or humanizing non-human or human antibodies can also be used and are well known in the art. Generally, a humanized or engineered antibody has one or more amino acid residues from a source which is non-human, e.g., but not limited to, mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., Kabat et al., Sequences of Proteins of Immunological Interest, U.S. Dept. Health (1983), which is entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. Generally part or all of the non-human or human CDR sequences are maintained while the non-human sequences of the variable and constant regions are replaced with human or other amino acids. Antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to those described in, Winter (Jones et al., 321 NATURE, 522 (1986); Riechmann et al., 332 NATURE, 323 (1988); Verhoeyen et al., 239 SCIENCE, 1534 (1988); Sims et al., 151 J. IMMUNOL., 2296 (1993); Chothia and Lesk, 196 J. MOL. BIOL., 901 (1987); Carter et al., 89 PROC. NATL. ACAD. SCI. U.S.A., 4285 (1992); Presta et al., 151 J. IMMUNOL., 2623 (1993); U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567; International Application Nos.: PCT/US98/16280; PCT/US96/18978; PCT/US91/09630; PCT/US91/05939; PCT/US94/01234; PCT/GB89/01334; PCT/GB91/01134; PCT/GB92/01755; International Publication Nos.: WO 90/14443; WO 90/14424; WO 90/14430; and European Patent Application No. EP 229246, each entirely incorporated herein by reference, including references cited therein.

The anti-Dengue virus antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-Dengue virus antibody can be isolated from such animals and immortalized using suitable methods, such as the methods described herein.

Transgenic mice that can produce a repertoire of human antibodies that bind to human antigens and other foreign antigens can be produced by known methods (e.g., but not limited to, U.S. Pat. Nos. 5,770,428; 5,569,825; 5,545,806; 5,625,126; 5,625,825; 5,633,425; 5,661,016 and 5,789,650 issued to Lonberg et al.; Jakobovits et al., WO 98/50433; Jakobovits et al., WO 98/24893; Lonberg et al., WO 98/24884; Lonberg et al., WO 97/13852; Lonberg et al., WO 94/25585; Kucherlapate et al., WO 96/34096; Kucherlapate et al., EP 0463151 B1; Kucherlapate et al., EP 0710719 A1; Surani et al., U.S. Pat. No. 5,545,807; Bruggemann et al., WO 90/04036; Bruggemann et al., EP 0438474 B1; Lonberg et al., EP 0814259 A2; Lonberg et al., GB 2272440 A; Lonberg et al., 368 NATURE, 856-859 (1994); Taylor et al., 6(4) INT. IMMUNOL., 579-591 (1994); Green et al, 7 NATURE GENETICS, 13-21 (1994); Mendez et al., 15 NATURE GENETICS, 146-156 (1997); Taylor et al., 20(23) NUCLEIC ACIDS RESEARCH, 6287-6295 (1992); Tuaillon et al., 90(8) PROC. NATL. ACAD. SCI. USA, 3720-3724 (1993); Lonberg et al., 13(1) INT. REV. IMMUNOL., 65-93 (1995) and Fishwald et al., 14(7) NAT BIOTECHNOL, 845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

The antigenic specificity of antibodies, for example those made by the methods described herein, can be conveniently determined using techniques known in the art, including, but not limited to, random peptide display libraries. This method involves the screening of large collections of peptides for individual members that are recognized by the antibody. Antibody screening of peptide display libraries is well known in the art. The displayed random peptide sequences can be from 3 to 5000 or more amino acids in length, frequently from 5 to 100 amino acids long, and often from about 8 to 25 amino acids long. In addition to direct chemical synthetic methods for generating peptide libraries, several recombinant DNA methods have been described. One type involves the display of random peptide sequences on the surface of a bacteriophage or cell. Each bacteriophage or cell contains the nucleotide sequence encoding the particular displayed peptide sequence. Antibody is immobilized on a substrate and incubated with bacteriophage or cells bearing the random peptide library on their surface. After several rounds of selection by panning as described for example in Lu et al., 13 BIO/TECHNOLOGY, 366-372 (1995), which is incorporated by reference herein, bacteriophage colonies are sequenced to determine the common peptide sequence recognized by the antibody. This method allows the identification of the antigen recognition sequence for the antibody. Such methods are described in PCT Patent Publication Nos. WO 91/18980, WO 91/19818, and WO 93/08278.

Another method well known in the art for identifying antibodies that are specific for a particular antigen is to utilize virus, bacteriophage or host cells expressing antibody molecules on their surface. In this method, DNA encoding the antibody or antibody fragment is contained within the virus, bacteriophage, host cell or other replication competent system. Portions of antibody molecules are expressed on the surface of the virus, bacteriophage, host cell or other replication competent system and are selected by binding to immobilized antigen. After several rounds of selection, the DNA encoding the antibody or antibody fragment is isolated. See PCT Patent Publication No. WO 91/17271. Other systems for generating libraries of random and specific peptides have aspects of both in vitro chemical synthesis and recombinant methods. See, PCT Patent Publication Nos. WO 92/05258, WO 92/14843, and WO 96/19256. See also, U.S. Pat. Nos. 5,658,754 and 5,643,768. Random peptide display libraries, antibody fragment display libraries, vectors, and screening kits for performing these methods are commercially available from such suppliers as Invitrogen (Carlsbad, Calif.), and Cambridge Antibody Technologies (Cambridgeshire, UK). See, e.g., U.S. Pat. Nos. 4,704,692; 4,874,702; 4,939,666; 4,946,778; 5,260,203; 5,455,030; 5,518,889; 5,534,621; 5,656,730; 5,763,733; 5,767,260; 5,856,456 are assigned to Enzon, U.S. Pat. Nos. 5,223,409; 5,403,484; 5,571,698 and 5,837,500 are assigned to Dyax; U.S. Pat. Nos. 5,427,908 and 5,580,717 are assigned to Affymax; U.S. Pat. No. 5,885,793 is assigned to Cambridge Antibody Technologies; U.S. Pat. No. 5,750,373 is assigned to Genentech; U.S. Pat. Nos. 5,618, 920; 5,595,898; 5,576,195; 5,698,435; 5,693,493 and 5,698, 417 are assigned to Xoma; Colligan, supra; Ausubel, supra; or Sambrook, supra, each of the above patents and publications entirely incorporated herein by reference.

Antibodies of the present invention can also be prepared using at least one anti-Dengue virus antibody-encoding nucleic acid to provide transgenic animals or mammals, such as goats, cows, horses, sheep, and the like, that produce such antibodies in their milk. Such animals can be provided using known methods. See, e.g., but not limited to, U.S. Pat. Nos. 5,827,690; 5,849,992; 4,873,316; 5,849,992; 5,994,616; 5,565,362 and 5,304,489, and the like, each of which is entirely incorporated herein by reference.

Antibodies of the present invention can additionally be prepared using at least one anti-Dengue virus antibody-encoding nucleic acid to provide transgenic plants and cultured plant cells (e.g., but not limited to tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., 240 CURR. TOP. MICROBOL. IMMUNOL., 95-118 (1999) and references cited therein. Also, transgenic maize have been used to express mammalian proteins at commercial production levels, with biological activities equivalent to those produced in other recombinant systems or purified from natural sources. See, e.g., Hood et al., 464 ADV. EXP. MED. BIOL., 127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., 38 PLANT MOL. BIOL., 101-109 (1998) and reference cited therein. Thus, antibodies of the present invention can also be produced using transgenic plants, according to known methods. See also, e.g., Fischer et al., 30 BIOTECHNOL. APPL. BIOCHEM., 99-108 (October, 1999), Ma et al., 13 TRENDS BIOTECHNOL., 522-527 (1995); Ma et al., 109 PLANT PHYSIOL., 341-346 (1995); Whitelam et al., 22 BIOCHEM. SOC. TRANS., 940-944 (1994); and references cited therein. Each of the above references is entirely incorporated herein by reference.

The antibodies of the invention can bind Dengue virus proteins with a wide range of affinities ($K_D$). In a preferred embodiment, at least one human mAb of the present invention can optionally bind Dengue virus NS1 protein with high affinity. For example, a human mAb can bind Dengue virus NS1 protein with a $K_D$ equal to or less than about $10^{-7}$ M, such as, but not limited to, 0.1 to 9.9 (or any range or value therein) X $10^{-7}$, $10^{-8}$, $10^{-9}$, $10^{-10}$, $10^{-11}$, $10^{-12}$ or any range or value therein.

The affinity or avidity of an antibody for an antigen can be determined experimentally using any suitable method. (See, for example, Berzofsky et al., "Antibody-Antigen Interactions," In *Fundamental Immunology*, (W. E. Paul (Ed.), Raven Press: New York, N.Y., 1984); Janis Kuby, *Immunology*, (W. H. Freeman and Company: New York, N.Y., 1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

The ability of the anti-Dengue virus antibodies described herein may also be tested for their ability to neutralize Dengue virus using virus neutralization procedures well known to those of ordinary skill in the art. Such virus neutralization procedures include, but are not limited to, those described in R. Rico-Hesse, "Molecular Evolution and Distribution of Dengue Viruses Type 1 and 2 in Nature", 174 VIROLOGY, 479-493 (1990); B. L. Innis, "Antibody Responses to Dengue Virus Infection", *Dengue and Dengue Hemorrhagic Fever*, (D. J. Gubler and G. Kuno (Eds.), CAB International, Cambridge (1997)) 221-243; Innis et al., "An Enzyme-Linked Immunosorbent Assay to Characterize Dengue Infections Where Dengue and Japanese Encephalitis Co-Circulate", 40 AM. J. TROP. MED. HYG., 418-427 (1989); and Kochel et al., "Neutralization of American Genotype Dengue 2 Viral Infection by Dengue 1 Antibodies May Have Prevented Dengue Hemorrhagic Fever in Iquitos, Peru", LANCET (2002), which are each incorporated by reference herein.

Nucleic Acid Molecules

Using the information provided herein, such as the nucleotide sequences encoding at least 70% to 100% of the contiguous amino acids of at least one of SEQ ID NOS: 3 and 4, specified fragments, variants or consensus sequences thereof, or a suitable vector comprising at least one of these sequences, a nucleic acid molecule of the present invention encoding at least one anti-Dengue virus antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain (e.g., SEQ ID NO: 1) or light chain (e.g., SEQ ID NO: 2); nucleic acid molecules comprising the coding sequence for an anti-Dengue virus antibody or variable region (e.g., SEQ ID NOS: 3 and 4); and nucleic acid molecules which comprise a nucleotide sequence substantially different from those described above but which, due to the degeneracy of the genetic code, still encode at least one anti-Dengue virus antibody as described herein and/or as known in the art. Of course, the genetic code is well known in the art. Thus, it would be routine for one skilled in the art to generate such degenerate nucleic acid variants that code for specific anti-Dengue virus antibodies of the present invention. See, e.g., Ausubel et al., supra, and such nucleic acid variants are included in the present invention. Non-limiting examples of isolated nucleic acid molecules of the present invention include SEQ ID NOS: 1 and 2.

As indicated herein, nucleic acid molecules of the present invention which comprise a nucleic acid encoding an anti-Dengue virus antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including, but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Construction of Nucleic Acids

The isolated nucleic acids of the present invention can be made using (a) recombinant methods, (b) synthetic techniques, (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

Recombinant Methods for Constructing Nucleic Acids

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra)

Synthetic Methods for Constructing Nucleic Acids

The isolated nucleic acids of the present invention can also be prepared by direct chemical synthesis by known methods (see, e.g., Ausubel et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention further provides recombinant expression cassettes comprising a nucleic acid of the present invention. A nucleic acid sequence of the present invention, for example a cDNA or a genomic sequence encoding an antibody of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution.

Vectors And Host Cells

The present invention also relates to vectors that include isolated nucleic acid molecules of the present invention, host cells that are genetically engineered with the recombinant vectors, and the production of at least one anti-Dengue virus antibody by recombinant techniques, as is well known in the art. See, e.g., Sambrook et al., supra; Ausubel et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome-binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636 and 5,179,017; ampicillin, neomycin (G418), mycophenolic acid, or glutamine synthetase (GS, U.S. Pat. Nos. 5,122,464; 5,770,359 and 5,827,739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the present invention.

Alternatively, nucleic acids of the present invention can be expressed in a host cell by turning on (by manipulation) expression in a host cell that contains endogenous DNA encoding an antibody of the present invention. Such methods are well known in the art, e.g., as described in U.S. Pat. Nos. 5,580,734; 5,641,670; 5,733,746 and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3×63Ag8.653, SP2/0-Agl4, 293 cells, HeLa cells and the like, which are readily available from, for example, American Type Culture Collection, Manassas, Va. In one embodiment, host cells include cells of lymphoid origin such as myeloma and lymphoma cells.

Expression vectors for these cells can include one or more of the following expression control sequences, such as, but not limited to, an origin of replication; a promoter (e.g., late or early SV40 promoters, the CMV promoter (US Pat. Nos. 5,168,062 and 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook et al., supra. Other cells useful for production of nucleic acids or proteins of the present invention are known and/or available, for instance, from the American Type Culture Collection Catalogue of Cell Lines and Hybridomas or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague et al., 45 J. VIROL., 773-781 (1983)). Additionally, gene sequences to control replication in the host cell can be incorporated into the vector, as known in the art.

Purification of an Antibody

An anti-Dengue virus antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, *Current Protocols in Immunology*, or *Current Protocols in Protein Science*, (John Wiley & Sons, New York, N.Y., 1997-2001), e.g., Chapters 1, 4, 6, 8, 9, 10, each entirely incorporated herein by reference.

Antibodies of the present invention include naturally purified products, products of chemical synthetic procedures, and products produced by recombinant techniques from a prokaryotic or eukaryotic host, including, for example, bacteria, fungiard, yeast, plant, insect, non-mammalian, and mammalian cells. Depending upon the host employed in a recombinant production procedure, the antibody of the present invention can be glycosylated or can be non-glycosylated, with glycosylated in certain embodiments. Such methods are described in many standard laboratory manuals, such as Sambrook, supra, Sections 17.37-17.42; Ausubel, supra, Chapters 10, 12, 13, 16, 18 and 20, Colligan, *Protein Science*, supra, Chapters 12-14, all entirely incorporated herein by reference.

Anti-Dengue Virus Antibodies

The isolated antibodies of the present invention comprise an antibody amino acid sequences disclosed herein encoded by any suitable polynucleotide, or any isolated or prepared antibody. The human antibody or antigen-binding fragment binds Dengue virus NS protein and thereby partially or substantially neutralizes at least one biological activity of the NS protein, or it may interfere with the replication cycle of the virus, or it may enhance the recognition of virus-infected cells by the host immune system which may facilitate killing of virus-infected cells and clearance of viral infection. The antibody of the present invention is not expected to cause the observed enhancement of Dengue virus infection as seen with antibodies that are specific for Dengue virus.[20, 21, 22, 23] An antibody, or specified portion or variant thereof, may partially or substantially neutralize at least one biological activity of at least one Dengue virus NS protein or fragment. The antibody may also bind the viral NS protein or fragment and thereby inhibit activities mediated through Dengue virus NS protein-dependent or NS protein-mediated mechanisms. Dengue virus infected cells present on their surface the Dengue virus NS proteins. In addition, since Dengue virus is an enveloped virus, these proteins may also be found in infective Dengue virus particle envelopes because the envelope is host cell derived. The antibody of the present invention may substantially increase the recognition of Dengue virus-infected cells by binding to the surface of Dengue virus-infected cell. Antibody bound to the surface of infected cells may facilitate antibody-dependent cellular cytotoxicity (ADCC) or cell dependent cytotoxicity (CDC) and thereby enhance the killing of virus-infected cells and interrupting the virus replication cycle. The interruption of the virus replication cycle may reduce the severity of infection and speed recovery from disease. The capacity of an anti-Dengue virus antibody to inhibit Dengue virus NS protein-dependent activity may be assessed by at least one suitable Dengue virus NS protein assay, an infectivity assay or a replication cycle assay, as described herein and/or as known in the art. An anti-Dengue virus antibody of the invention can be of any class (IgG, IgA, IgM, IgE, IgD, etc.) or isotype and can comprise a kappa or lambda light chain. In one embodiment, the antibody comprises an IgG heavy chain or defined fragment, for example, at least one of isotypes IgG1, IgG2, IgG3 or IgG4. Antibodies of this type can be prepared by employing a transgenic mouse or other trangenic non-human mammal comprising at least one human light chain (e.g., IgG, IgA and IgM (e.g., $\gamma 1$, $\gamma 2$, $\gamma 3$, $\gamma 4$) transgenes as described herein and/or as known in the art. In another embodiment, the anti-Dengue virus antibody comprises an IgG1 heavy chain and a IgG1 light chain.

At least one antibody of the invention binds at least one specified epitope specific to at least one Dengue virus protein, subunit, fragment, portion or any combination thereof. At least one epitope can comprise at least one antibody binding region that comprises at least one portion of said protein, which epitope is preferably comprised of at least one extracellular, structural, non-structural, soluble, hydrophilic, external or cytoplasmic portion of said protein. The at least one specified epitope can comprise any combination of at least one amino acid sequence of at least one to three amino acids, to the entire specified portion of contiguous amino acids of the Dengue virus protein.

Generally, the human antibody or antigen-binding fragment of the present invention will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. As a non-limiting example, the antibody or antigen-binding portion or variant can comprise at least one of the heavy chain CDR3 having the amino acid sequence of SEQ ID NO: 3, and/or a light chain CDR3 having the amino acid sequence of SEQ ID NO: 4. In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2 and/or 3 (e.g., SEQ ID NO: 3). In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3 (e.g., SEQ ID NO: 4). In a preferred embodiment the three heavy chain CDRs and the three light chain CDRs of the antibody or antigen-binding fragment have the amino acid sequence of the corresponding CDR of at least one of mAb (such as the anti-dengue virus antibody referred to herein as DEN3, which is not to be confused with the Dengue virus serotype 3 known as DEN-3), as described herein. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

The anti-Dengue virus antibody can comprise at least one of a heavy or light chain variable region having a defined amino acid sequence. For example, in a preferred embodiment, the anti-Dengue virus antibody comprises at least one of at least one heavy chain variable region, optionally having the amino acid sequence of SEQ ID NO: 3 and/or at least one light chain variable region, optionally having the amino acid sequence of SEQ ID NO: 4. Antibodies that bind to Dengue virus and that comprise a defined heavy or light chain variable region can be prepared using suitable methods, such as phage display (Katsube et al., 1(5) INT. J. MOL. MED., 863-868 (1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with Dengue virus or a fragment thereof to elicit the production of antibodies. If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

The invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind Dengue virus with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Amino Acid Codes

The amino acids that make up anti-Dengue virus antibodies of the present invention are often abbreviated. The amino acid designations can be indicated by designating the amino acid by its single letter code, its three letter code, name, or three nucleotide codon(s) as is well understood in the art (see Alberts et al., *Molecular Biology of The Cell* 3rd *Edition*, (Garland Publishing, Inc., New York, (1994)):

| Single Letter Code | Three Letter Code | Name | Three Nucleotide Codon(S) |
|---|---|---|---|
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, GAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

An anti-Dengue virus antibody of the present invention can include one or more amino acid substitutions, deletions or additions, either from natural mutations or human manipulation, as specified herein.

Of course, the number of amino acid substitutions a skilled artisan would make depends on many factors, including those described above. Generally speaking, the number of amino acid substitutions, insertions or deletions for any given anti-Dengue virus antibody, fragment or variant will not be more than 40, 30, 20, 19, 18, 17, 16, 15, 14, 13, 12, 11, 10, 9, 8, 7, 6, 5, 4, 3, 2, 1, such as 1 to 30 or any range or value therein, as specified herein.

Amino acids in an anti-Dengue virus antibody of the present invention that are essential for function can be identified by methods known in the art, such as site-directed mutagenesis or alanine-scanning mutagenesis (e.g., Ausubel, supra, Chapters 8, 15; Cunningham and Wells, 244 SCIENCE, 1081-1085 (1989)). The latter procedure introduces single alanine mutations at every residue in the molecule. The resulting mutant molecules are then tested for biological activity, such as, but not limited to, at least one Dengue virus NS protein binding activity. Sites that are critical for antibody binding can also be identified by structural analysis such as crystallization, nuclear magnetic resonance or photoaffinity labeling (Smith et al., 224 J. MOL. BIOL., 899-904 (1992), and de Vos et al., 255 SCIENCE, 306-312 (1992)).

Anti-Dengue virus antibodies of the present invention can include, but are not limited to, at least one portion, sequence or combination selected from five to all of the contiguous amino acids of at least one of SEQ ID NOS: 3 and 4.

A(n) anti-Dengue virus antibody can further optionally comprise a polypeptide of at least one of 70% to 100% of the contiguous amino acids of at least one of SEQ ID NOS: 3 and 4.

In one embodiment, the amino acid sequence of an immunoglobulin chain, or portion thereof (e.g., variable region, CDR) has about 70% to 100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of SEQ ID NO: 4. For example, the amino acid sequence of a light chain variable region can be compared with the sequence of SEQ ID NO: 4, or the amino acid sequence of a heavy chain CDR3 can be compared with SEQ ID NO: 3. Preferably, 70% to 100% amino acid identity (i.e., 90, 91, 92, 93, 94, 95, 96, 97, 98, 99, 100 or any range or value therein) is determined using a suitable computer algorithm, as known in the art.

Exemplary heavy chain and light chain variable regions sequences are provided in SEQ ID NOS: 3 and 4. The antibodies of the present invention, or specified variants thereof, can comprise any number of contiguous amino acid residues from an antibody of the present invention, wherein that number is selected from the group of integers consisting of from 10% to 100% of the number of contiguous residues in an anti-Dengue virus antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4 or 5.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-$\Delta$9-octadecanoate ($C_{18}$, oleate), all cis-$\Delta$5,8,11,14-eicosatetraenoate ($C_{20}$, arachidonate), octanedioic acid, tetradecanedioic acid, octadecanedioic acid, docosanedioic acid, and the like. Suitable fatty acid esters include monoesters of dicarboxylic acids that comprise a linear or branched lower alkyl group. The lower alkyl group can comprise from one to about twelve, preferably one to about six, carbon atoms.

The modified antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, G. T. Hermanson, *Bioconiugate Techniques*, (Academic Press, San Diego, Calif. (1996)). An activating group can be bonded directly to the organic group (e.g., hydrophilic polymer, fatty acid, fatty acid ester), or through a linker moiety, for example a divalent $C1-C_{12}$ group wherein one or more carbon atoms can be replaced by a heteroatom such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221, the entire teachings of which are incorporated herein by reference.)

The modified antibodies of the invention can be produced by reacting an antibody or antigen-binding fragment with a modifying agent. For example, the organic moieties can be bonded to the antibody in a non-site specific manner by employing an amine-reactive modifying agent, for example, an NHS ester of PEG. Modified antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified antibodies and antigen-binding fragments comprising an organic moiety that is bonded to specific sites of an antibody of the present invention can be prepared using suitable methods, such as reverse proteolysis (Fisch et al., 3 BIOCONJUGATE CHEM., 147-153 (1992); Werlen et al., 5 BIOCONJUGATE CHEM., 411-417 (1994); Kumaran et al., 6(10) PROTEIN SCI., 2233-2241 (1997); Itoh et al., 24(1) BIOORG. CHEM., 59-68 (1996); Capellas et al., 56(4) BIOTECHNOL. BIOENG., 456-463 (1997)), and the methods described in G. T. Hermanson, *Bioconjugate Techniques*, (Academic Press, San Diego, Calif. (1996)).

Anti-Dengue Virus Antibody Compositions

The present invention also provides at least one anti-Dengue virus antibody composition comprising at least one, at least two, at least three, at least four, at least five, at least six or more anti-Dengue virus antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-Dengue virus antibody amino acid sequence selected from the group consisting of 70% to 100% of the contiguous amino acids of SEQ ID NOS: 3 and 4 or specified fragments, domains or variants thereof. Preferred anti-Dengue virus antibody compositions include at least one or two full length, fragments, domains or variants as at least one CDR or LBR containing portions of the anti-Dengue virus antibody sequence of 70% to 100% of SEQ ID NOS: 3 or 4 or specified fragments, domains or variants thereof. Further preferred compositions comprise 40% to 99% of at least one of 70% to 100% of SEQ ID NOS: 3 or 4 or specified fragments, domains or variants thereof. Such composition percentages are by weight, volume, concentration, molarity, or molality as liquid or dry solutions, mixtures, suspension, emulsions or colloids, as known in the art or as described herein.

Anti-Dengue virus antibody compositions of the present invention can further comprise at least one of any suitable and effective amount of a composition or pharmaceutical composition comprising at least one anti-Dengue virus antibody to a cell, tissue, organ, animal or patient in need of such modulation, treatment or therapy, optionally further comprising at least one selected from at least one Dengue virus anti-viral agent (e.g., but not limited to, an anti-Dengue virus antibody or fragment, a soluble Dengue virus receptor or fragment, fusion proteins thereof, or a small molecule Dengue virus infectivity or replication antagonist), an anti-rheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a growth factor cytokine or a growth factor cytokine antagonist. Non-limiting examples of such growth factors or cytokines include, but are not limited to, any of Erythropoietin, interferons, GCSF, GMCSF, and IL-1 to IL-23. Suitable dosages are well known in the art. See, e.g., Wells et al. (Eds.), *Pharmacotherapy Handbook, 2$^{nd}$ Edition*, (Appleton and Lange, Stamford, Conn. (2000)); *PDR Pharmacopoeia, Tarascon Pocket Pharmacopoeia 2000, Deluxe Edition*, (Tarascon Publishing, Loma Linda, Calif. (2000)), each of which references are entirely incorporated herein by reference.

Such anti-cancer, anti-viral or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), *Staphylococcal* enterotoxin A (SEA), B (SEB), or C (SEC), *Streptococcal* enterotoxins and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii*, and *Shigella sonnei*), *Salmonella* species (e.g., *Salmonella typhi, Salmonella choleraesuis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios parahemolyticus*), *Klebsiella* species, *Pseudomonas aeruginosa*, and *Streptococci*. See, e.g., Stein, ed., *Internal Medicine, 3$^{rd}$ Edition*, pp 1-13, (Little, Brown and Co., Boston, Mass. (1990)); Evans et al. (Eds.), *Bacterial Infections of Humans: Epidemiology and*

Control, 2*nd* Edition, pp 239-254, (Plenum Medical Book Co., New York, N.Y. (1991)); Mandell et al, *Principles and Practice of Infectious Diseases*, 3*rd* Edition, (Churchill Livingstone, New York, N.Y. (1990)); Berkow et al. (Eds.), *The Merck Manual*, 16*th* Edition, (Merck and Co., Rahway, N.J., (1992)); Wood et al, 76 FEMS MICROBIOLOGY IMMUNOLOGY, 121-134 (1991); Marrack et al, 248 SCIENCE, 705-711 (1990), the contents of which references are incorporated entirely herein by reference.

Anti-Dengue virus antibody compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro (Ed.), *Remington's Pharmaceutical Sciences* 18*th* Edition, (Mack Publishing Co., Easton, Pa. (1990)). Pharmaceutically acceptable carriers can be routinely selected that are suitable for the mode of administration, solubility and/or stability of the anti-Dengue virus antibody, fragment or variant composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1% to 99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-Dengue virus antibody compositions can also include a buffer or a pH-adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, anti-Dengue virus antibody compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-Dengue virus antibody, portion or variant compositions according to the invention are known in the art, e.g., as listed in *Remington: The Science & Practice of Pharmacy*, 19*th* Edition, (Williams & Williams, (1995)), and in the *Physician's Desk Reference*, 52*nd* Edition, (Medical Economics, Montvale, N.J. (1998)), the disclosures of which are entirely incorporated herein by reference. Preferred carrier or excipient materials are carbohydrates (e.g., saccharides and alditols) and buffers (e.g., citrate) or polymeric agents.

Formulations

As noted above, the invention provides for stable formulations, which is preferably a phosphate buffer with saline or a chosen salt, as well as preserved solutions and formulations containing a preservative as well as multi-use preserved formulations suitable for pharmaceutical or veterinary use, comprising at least one anti-Dengue virus antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001% to 5%, or any range or value therein, such as, but not limited to 0.001, 0.003, 0.005, 0.009, 0.01, 0.02, 0.03, 0.05, 0.09, 0.1, 0.2, 0.3, 0.4., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1% to 2% m-cresol (e.g., 0.2, 0.3, 0.4, 0.5, 0.9, 1.0%), 0.1% to 3% benzyl alcohol (e.g., 0.5, 0.9, 1.1., 1.5, 1.9, 2.0, 2.5%), 0.001% to 0.5% thimerosal (e.g., 0.005, 0.01), 0.001-2.0% phenol (e.g., 0.05, 0.25, 0.28, 0.5, 0.9, 1.0%), 0.0005% to 1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one anti-Dengue virus antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one anti-Dengue virus antibody, and a second vial comprising an aqueous diluent of prescribed buffer or preservative, wherein said packaging material comprises a label that instructs a patient to reconstitute the at least one anti-Dengue virus antibody in the aqueous diluent to form a solution that can be held over a period of twenty-four hours or greater.

The at least one anti-Dengue virus antibody used in accordance with the present invention can be produced by recombinant means, including from mammalian cell or transgenic preparations, or can be purified from other biological sources, as described herein or as known in the art.

The range of at least one anti-Dengue virus antibody in the product of the present invention includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one anti-Dengue virus antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-Dengue virus antibody and preservative in an aqueous diluent is carried out using conventional dissolution and mixing procedures. To prepare a suitable formulation, for example, a measured amount of at least one anti-Dengue virus antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized at least one anti-Dengue virus antibody that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2° C. to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to one to twelve months, one-half, one and a half, and/or two years.

The solutions of at least one anti-Dengue virus antibody in the invention can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-Dengue virus antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-Dengue virus antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising these single vial systems include those pen-injector devices for delivery of a solution such as BD Pens, BD Autojector®, Humaject®, NovoPen®, B-D®Pen, AutoPen®, and OptiPen®, GenotropinPen®, Genotronorm Pen®, Humatro Pen®, Reco-Pen®, Roferon Pen®, Biojector®, iject®, J-tip Needle-Free Injector®, Intraject®, Medi-Ject®, e.g., as made or developed by Becton Dickensen (Franklin Lakes, N.J.), Disetronic (Burgdorf, Switzerland; Bioject (Portland, Oreg.); National Medical Products, Weston Medical (Peterborough, United Kingdom), and Medi-Ject Corporation (Minneapolis, Minn.). Recognized devices comprising a dual vial system include those pen-injector systems for reconstituting a lyophilized drug in a cartridge for delivery of the reconstituted solution such as the HumatroPen®.

The products presently claimed include packaging material. The packaging material provides, in addition to the information required by the regulatory agencies, the conditions under which the product can be used. The packaging material of the present invention provides instructions to the patient to reconstitute the at least one anti-Dengue virus antibody in the aqueous diluent to form a solution and to use the solution over a period of two to twenty-four hours or greater for the two vial, wet/dry, product. For the single vial, solution product, the label indicates that such solution can be used over a period of two to twenty-four hours or greater. The presently claimed products are useful for human pharmaceutical product use.

The formulations of the present invention can be prepared by a process that comprises mixing at least one anti-Dengue virus antibody and a selected buffer, preferably a phosphate buffer containing saline or a chosen salt. Mixing the at least one antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one anti-Dengue virus antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

At least one anti-Dengue virus antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

The present invention also provides a method for modulating or treating at least one Dengue virus related disease or condition, in a cell, tissue, organ, animal, or patient, as known in the art or as described herein, using at least one anti-Dengue virus antibody of the present invention. The present invention also provides methods for modulating, treating or preventing Dengue virus infection in a subject. The present invention also provides methods for modulating, treating, inhibiting or blocking Dengue virus infectivity or replication in a cell, tissue, organ, animal or patient.

Any method of the present invention can comprise administering an effective amount of a composition or pharmaceutical composition comprising at least one anti-Dengue virus antibody to a cell, tissue, organ, animal or patient in need of such modulation, treatment, prevention or therapy. Such a method can optionally further comprise co-administration or combination therapy for such modulation, treatment, prevention or therapy, wherein the administering of said at least one anti-Dengue virus antibody, specified portion or variant thereof, further comprises administering, before, concurrently, and/or after, at least one agent selected from at least one Dengue virus antagonist (e.g., but not limited to, a Dengue virus antibody or fragment, a soluble Dengue virus receptor or fragment, fusion proteins thereof, or a small molecule Dengue virus antagonist), an anti-rheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an anti-infective agent, an anti-tumor agent, an antiproliferative agent, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonist. Suitable dosages are well known in the art. See, e.g., Wells et al. (Eds.), *Pharmacotherapy Handbook. $2^{nd}$ Edition*, (Appleton and Lange, Stamford, Conn. (2000)); and *PDR Pharmacopoeia, Tarascon Pocket Pharmacopoeia* 2000, *Deluxe Edition*, (Tarascon Publishing, Loma Linda, Calif. (2000)), each of which references are entirely incorporated herein by reference.

As used herein, an "Anti-Dengue virus antibody" or fragment and the like decreases, blocks, inhibits, abrogates or interferes with Dengue virus activity infectivity or replication, in vitro, in situ and/or preferably in vivo. For example, a suitable Dengue virus antibody of the present invention can bind Dengue virus or Dengue virus-infected cells and includes whole anti-Dengue virus antibodies, antigen-binding fragments thereof, and specified mutants or domains thereof that bind specifically to Dengue virus or Dengue virus infected cells. A suitable Dengue virus antibody or fragment can also decrease, block, abrogate, interfere, prevent and/or inhibit Dengue virus RNA, DNA or protein synthesis, Dengue virus release, Dengue virus cell receptor interaction, membrane Dengue virus cleavage, Dengue virus activity, Dengue virus replication, production and/or synthesis.

Preferred methods for determining monoclonal antibody specificity and affinity by competitive inhibition can be found in Harlow et al., *Antibodies: A Laboratory Manual*, (Cold Spring Harbor Laboratory Press, Cold Spring Harbor, N.Y., (1988)); Colligan et al. (Eds.), *Current Protocols in Immunology*, (Greene Publishing Assoc. and Wiley Interscience, New York, (1992-2000)); Kozbor et al., 4 IMMUNOL. TODAY, 72-79 (1983); Ausubel et al. (Eds.), *Current Protocols in Molecular Biology*, (Wiley Interscience, New York (1987-2000)); and Muller, 92 METH. ENZYMOL., 589-601 (1983)), which references are entirely incorporated herein by reference.

Cytokines include any known cytokine. Cytokine antagonists include, but are not limited to, any antibody, fragment or mimetic, any soluble receptor, fragment or mimetic, any small molecule antagonist, or any combination thereof.

Typically, treatment of pathologic conditions is effected by administering an effective amount or dosage of at least one anti-Dengue virus antibody composition that total, on average, a range from at least about 0.01 to 500 milligrams of at least one anti-Dengue virus antibody per kilogram of patient per dose, and preferably from at least about 0.1 to 100 milligrams antibody/kilogram of patient per single or multiple administration, depending upon the specific activity of contained in the composition. Alternatively, the effective serum concentration can comprise 0.1 to 5000 µg/ml serum concentration per single or multiple administration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100 to 500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5., 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.1 milligram to about 500 milligrams of active ingredient per unit or container. In these pharmaceutical compositions the active ingredient will ordinarily be present in an amount of about 0.5 to 99.999% by weight based on the total weight of the composition.

For parenteral administration, the antibody can be formulated as a solution, suspension, emulsion or lyophilized powder in association, or separately provided, with a pharmaceutically acceptable parenteral vehicle. Examples of such vehicles are water, saline, Ringer's solution, dextrose solution, and 1% to 10% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Parenteral Formulations and Administration

Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semi-synthetic fatty oils or fatty acids; natural or synthetic or semi-synthetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446 entirely incorporated herein by reference.

Delivery

The invention further relates to the administration of at least one anti-Dengue virus antibody by parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means. At least one anti-Dengue virus antibody composition can be prepared for use for parenteral (subcutaneous, intramuscular or intravenous) or any other administration particularly in the form of liquid solutions or suspensions; for use in vaginal or rectal administration particularly in semisolid forms such as, but not limited to, creams and suppositories; for buccal, or sublingual administration such as, but not limited to, in the form of tablets or capsules; or intranasally such as, but not limited to, the form of powders, nasal drops or aerosols or certain agents; or transdermally such as not limited to a gel, ointment, lotion, suspension or patch delivery system with chemical enhancers such as dimethyl sulfoxide to either modify the skin structure or to increase the drug concentration in the transdermal patch (Junginger et al., *Drug Permeation Enhancement*, pp. 59-90 (D. S. Hsieh (Ed.), Marcel Dekker, Inc., New York (1994)), entirely incorporated herein by reference), or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

Pulmonary/Nasal Administration

For pulmonary administration, preferably at least one anti-Dengue virus antibody composition is delivered in a particle size effective for reaching the lower airways of the lung or sinuses. According to the invention, at least one anti-Dengue virus antibody can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use of formulations suitable for the administration for the dispensing of antibody in an aerosol. Such aerosols can be comprised of either solutions (both aqueous and non aqueous) or solid particles. Metered dose inhalers like the Ventolin® metered dose inhaler, typically use a propellant gas and require actuation during inspiration (See, e.g., International Publication Nos. WO 94/16970 and WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218, Astra; EP 237507, Astra; International Publication No. WO 97/25086, Glaxo; International Publication No. WO 94/08552, Dura; U.S. Pat. No. 5,458,135, Inhale; and International Publication No. WO 94/06498, Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404,871, Aradigm; and International Publication No. WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention. Preferably, a composition comprising at least one anti-Dengue virus antibody is delivered by a dry powder inhaler or a sprayer. There are a several desirable features of an inhalation device for administering at least one antibody of the present invention. For example, delivery by the inhalation device is advantageously reliable, reproducible, and accurate. The inhalation device can optionally deliver small dry particles, e.g. less than about 10 μm, preferably about 1 to 5 μm, for good respirability.

Administration of Anti-Dengue Virus Antibody Compositions as a Spray

A spray including Dengue virus antibody composition protein can be produced by forcing a suspension or solution of at least one anti-Dengue virus antibody through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one anti-Dengue virus antibody composition protein delivered by a sprayer have a particle size less than about 10 μm, preferably in the range of about 1 μm to about 5 μm, and most preferably about 2 μm to about 3 μm.

Formulations of at least one anti-Dengue virus antibody composition protein suitable for use with a sprayer typically include antibody composition protein in an aqueous solution at a concentration of about 0.1 mg to about 100 mg of at least one anti-Dengue virus antibody composition protein per ml of solution or mg/gm, or any range or value therein, e.g., but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The formulation can include agents such as an excipient, a buffer, an isotonicity agent, a preservative, a surfactant, and, preferably, zinc. The formulation can also include an excipient or agent for stabilization of the antibody composition protein, such as a buffer, a reducing agent, a bulk protein, or a carbohydrate. Bulk proteins useful in formulating antibody composition proteins include albumin, protamine, or the like. Typical carbohydrates useful in formulating antibody composition proteins include sucrose, mannitol, lactose, trehalose, glucose, or the like. The antibody composition protein formulation can also include a surfactant, which can reduce or prevent surface-induced aggregation of the antibody composition protein caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001% and 14% by weight of the formulation. Especially preferred surfactants for purposes of this invention are polyoxyethylene sorbitan monooleate, polysorbate 80, polysorbate 20, or the like. Additional agents known in the art for formulation of a protein such as anti-Dengue virus antibodies, or specified portions or variants, can also be included in the formulation.

Administration of Dengue Virus Antibody Compositions by a Nebulizer

Antibody composition protein can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition protein either directly or through a coupling fluid, creating an aerosol including the antibody composition protein. Advantageously, particles of antibody composition protein delivered by a nebulizer have a particle size less than about 10 μm, preferably in the range of about 1 μm to about 5 μm, and most preferably about 2 μm to about 3 μm.

Formulations of at least one anti-Dengue virus antibody suitable for use with a nebulizer, either jet or ultrasonic, typically include a concentration of about 0.1 mg to about 100 mg of at least one anti-Dengue virus antibody protein per ml of solution. The formulation can include agents such as an excipient, a buffer, an isotonicity agent, a preservative, a surfactant, and, preferably, zinc. The formulation can also include an excipient or agent for stabilization of the at least one anti-Dengue virus antibody composition protein, such as a buffer, a reducing agent, a bulk protein, or a carbohydrate. Bulk proteins useful in formulating at least one anti-Dengue virus antibody composition proteins include albumin, protamine, or the like. Typical carbohydrates useful in formulating at least one anti-Dengue virus antibody include sucrose, mannitol, lactose, trehalose, glucose, or the like. The at least one anti-Dengue virus antibody formulation can also include a surfactant, which can reduce or prevent surface-induced aggregation of the at least one anti-Dengue virus antibody caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein such as antibody protein can also be included in the formulation.

Administration of Dengue Virus Antibody Compositions by a Metered Dose Inhaler

In a metered dose inhaler (MDI), a propellant, at least one anti-Dengue virus antibody, and any excipients or other additives are contained in a canister as a mixture including a liquefied compressed gas. Actuation of the metering valve releases the mixture as an aerosol, preferably containing particles in the size range of less than about 10 μm, preferably about 1 μm to about 5 μm, and most preferably about 2 μm to about 3 μm. The desired aerosol particle size can be obtained by employing a formulation of antibody composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of at least one anti-Dengue virus antibody for use with a metered-dose inhaler device will generally include a finely divided powder containing at least one anti-Dengue virus antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like. Preferably the propellant is a hydrofluorocarbon. The surfactant can be chosen to stabilize the at least one anti-Dengue virus antibody as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein such as protein can also be included in the formulation.

One of ordinary skill in the art will recognize that the methods of the current invention can be achieved by pulmonary administration of at least one anti-Dengue virus antibody compositions via devices not described herein.

Oral Formulations and Administration

Formulations for oral administration may rely on the co-administration of adjuvants (e.g., resorcinols and nonionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semi-synthetic polymer, and glyceride. These dosage forms can also contain other type(s) of additives, e.g., inactive diluting agent, lubricant such as magnesium stearate, paraben, preserving agent such as sorbic acid, ascorbic acid, α-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925,673). Furthermore, carrier compounds described in U.S. Pat. Nos. 5,879,681 and 5,871,753 are used to deliver biologically active agents orally are known in the art.

Mucosal Formulations and Administration

For absorption through mucosal surfaces, compositions and methods of administering at least one anti-Dengue virus antibody include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like (U.S. Pat. No. 5,849,695).

Transdermal Formulations and Administration

For transdermal administration, the at least one anti-Dengue virus antibody is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

Prolonged Administration and Formulations

It can be sometimes desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g. a zinc tannate salt. Additionally, the compounds of the present invention or, preferably, a relatively insoluble salt such as those just described, can be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above can also be formulated in cholesterol matrix silastic pellets, particularly for use in animals. Additional slow release, depot or implant formulations, e.g. gas or liquid liposomes are known in the literature (U.S. Pat. No. 5,770,222 and *Sustained and Controlled Release Drug Delivery Systems*, (J. R. Robinson (Ed.), Marcel Dekker, Inc., New York (1978)).

Having generally described the invention, the same will be more readily understood by reference to the following examples, which are provided by way of illustration and are not intended as limiting.

EXAMPLE 1

Cloning and Expression of Dengue Virus Antibody in Mammalian Cells

A typical mammalian expression vector contains at least one promoter element, which mediates the initiation of transcription of mRNA, the antibody coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pIRES1neo, pRetro-Off, pRetro-On, PLXSN, or pLNCX (Clonetech Labs, Palo Alto, California), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy et al., 227 BIOCHEM. J., 277-279 (1991); and Bebbington et al., 10 BIO/TECHNOLOGY, 169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

The expression vectors pC1 and pC4 contain the strong promoter (LTR) of the Rous Sarcoma Virus (Cullen et al., 5 MOLEC. CELL. BIOL., 438-447 (1985)) plus a fragment of the CMV-enhancer (Boshart et al., 41 CELL, 521-530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Cloning and Expression in CHO Cells

The vector pC4 may be used for the expression of Dengue virus antibody. Plasmid pC4 is a derivative of the plasmid pSV2-dhfr (ATCC Accession No. 37146). The plasmid contains the mouse DHFR gene under control of the SV40 early promoter. Chinese hamster ovary or other cells lacking dihydrofolate activity that are transfected with these plasmids can be selected by growing the cells in a selective medium (e.g., alpha minus MEM, Life Technologies, Gaithersburg, Md.) supplemented with the chemotherapeutic agent methotrexate. The amplification of the DHFR genes in cells resistant to methotrexate (MTX) has been well documented (see, e.g., Alt et al., 253 J. BIOL. CHEM., 1357-1370 (1978); J. L. Hamlin and C. Ma, 1097 BIOCHEM. ET BIOPHYS. ACTA, 107-143 (1990); and M. J. Page and M. A. Sydenham, 9 BIOTECHNOLOGY, 64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Plasmid pC4 contains for expressing the gene of interest the strong promoter of the long terminal repeat (LTR) of the Rous Sarcoma Virus (Cullen et al., 5 MOLEC. CELL. BIOL., 438-447 (1985)) plus a fragment isolated from the enhancer of the immediate early gene of human cytomegalovirus (CMV) (Boshart et al., 41 CELL, 521-530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human b-actin promoter, the SV40 early or late promoters or the long terminal repeats from other retroviruses, e.g., HIV and HTLVI. Clontech's Tet-Off and Tet-On gene expression systems and similar systems can be used to express the Dengue virus in a regulated way in mammalian cells (M. Gossen and H. Bujard, 89 PROC. NATL. ACAD. SCI. USA, 5547-5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with restriction enzymes and then dephosphorylated using calf intestinal phosphatase by procedures known in the art. The vector is then isolated from a 1% agarose gel.

The isolated variable and constant region encoding DNA and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary (CHO) cells lacking an active DHFR gene are used for transfection. 5 μg of the expression plasmid pC4 is co-transfected with 0.5 μg of the plasmid pSV2-neo using lipofectin. The plasmid pSV2neo contains a dominant selectable marker, the neo gene from Tn5 encoding an enzyme that confers resistance to a group of antibiotics including G418. The cells are seeded in alpha minus MEM supplemented with 1 μg/ml G418. After two days, the cells are trypsinized and seeded in hybridoma cloning plates (Greiner, Germany) in alpha minus MEM supplemented with 10, 25, or 50 ng/ml of methotrexate plus 1 μg/ml G418. After about ten to fourteen days, single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained that grow at a concentration of 100-200 mM. Expression of the desired gene product is analyzed, for instance, by SDS-PAGE and Western blot or by reverse phase HPLC analysis.

EXAMPLE 2

Generation of High Affinity Human IgG Monoclonal Antibodies Reactive with Human Dengue Virus Using Transgenic Mice Transgenic mice may be used that contain human heavy and light chain immunoglobulin genes to generate high affinity, completely human, monoclonal antibodies that can be used therapeutically to inhibit the action of Dengue virus for the treatment of one or more Dengue virus-mediated disease. (CBA/J×C57/BL6/J) $F_2$ hybrid mice containing human variable and constant region antibody transgenes for both heavy and light chains are immunized with human recombinant Dengue virus (Taylor et al., 6 INTL. IMMUNOL., 579-591 (1993); Lonberg et al., 368 NATURE, 856-859 (1994); M. Neuberger, 14 NATURE BIOTECH., 826 (1996); Fishwild et al., 14 NATURE BIOTECHNOLOGY, 845-851 (1996)). Several fusions yielded one or more panels of completely human Dengue virus reactive IgG monoclonal antibodies. The completely human anti-Dengue virus antibodies are further characterized. Such antibodies are found to have affinity constants somewhere between $1\times10^9$ and $9\times10^{12}$. The unexpectedly high affinities of these fully human monoclonal antibodies make them suitable candidates for therapeutic applications in Dengue virus related diseases, pathologies or disorders.

| Abbreviations | |
|---|---|
| BSA | bovine serum albumin |
| $CO_2$ | carbon dioxide |
| DMSO | dimethyl sulfoxide |
| EIA | enzyme immunoassay |
| FBS | fetal bovine serum |
| $H_2O_2$ | hydrogen peroxide |
| HRP | horseradish peroxidase |
| ID | Interadermal |
| Ig | Immunoglobulin |
| IP | Intraperitoneal |
| IV | Intravenous |
| mAb | monoclonal antibody |
| OD | optical density |
| OPD | o-Phenylenediamine dihydrochloride |
| PEG | polyethylene glycol |
| PSA | penicillin, streptomycin, amphotericin |
| RT | room temperature |
| SQ | Subcutaneous |
| TNF∀ | tissue necrosis factor alpha |
| v/v | volume per volume |
| w/v | weight per volume |

Materials and Methods

Animals

Transgenic mice that can express human antibodies are known in the art (and are commercially available (e.g., from Medarex San Jose, Calif.; Abgenix, Freemont, Calif., and others) that express human immunoglobulins, but not mouse IgM or Igκ. For example, such transgenic mice contain human sequence transgenes that undergo V(D)J joining, heavy-chain class switching, and somatic mutation to generate a repertoire of human sequence immunoglobulins (Lonberg et al., 368 NATURE, 856-859 (1994)). The light chain transgene can be derived, e.g., in part from a yeast artificial chromosome clone that includes nearly half of the germline human Vκ region. In addition, the heavy-chain transgene can encode both human μ and human γ1 (Fishwild et al., 14 NATURE BIOTECHNOLOGY, 845-851 (1996)) and/or γ3 constant regions. Mice derived from appropriate genotopic lineages can be used in the immunization and fusion processes to generate fully human monoclonal antibodies to Dengue virus.

Immunization

One or more immunization schedules can be used to generate the anti-Dengue virus human hybridomas. The first several fusions can be performed after the following exemplary immunization protocol, but other similar known protocols can be used. Several fourteen to twenty week-old female and/or surgically castrated transgenic male mice are immunized IP and/or ID with 1 to 1000 μg of recombinant human Dengue virus emulsified with an equal volume of TITERMAX or complete Freund's adjuvant in a final volume of 100 to 400 μL (e.g., 200). Each mouse can also optionally receive 1 to 10 μg in 100 μL physiological saline at each of two SQ sites. The mice can then be immunized 1 to 7, 5 to 12, 10 to 18, 17 to 25 and/or 21 to 34 days later IP (1 to 400 μg) and SQ (1 to 400 μg×2) with Dengue virus emulsified with an equal volume of TITERMAX or incomplete Freund's adjuvant. Mice can be bled 12 to 25 and 25 to 40 days later by retro-orbital puncture without anti-coagulant. The blood is then allowed to clot at room temperature for one hour and the serum is collected and titered using an Dengue virus EIA assay according to known methods. Fusions are performed when repeated injections do not cause titers to increase. At that time, the mice can be given a final IV booster injection of 1 to 400 μg Dengue virus diluted in 100 μL physiological saline. Three days later, the mice can be euthanized by cervical dislocation and the spleens removed aseptically and immersed in 10 mL of cold phosphate buffered saline (PBS) containing 100 U/mL penicillin, 100 μg/mL streptomycin, and 0.25 μg/mL amphotericin B (PSA). The splenocytes are harvested by sterilely perfusing the spleen with PSA-PBS. The cells are washed once in cold PSA-PBS, counted using Trypan blue dye exclusion and re-suspended in RPMI 1640 media containing 25 mM Hepes.

Cell Fusion

Fusion can be carried out at a 1:1 to 1:10 ratio of murine myeloma cells to viable spleen cells according to known methods, e.g., as known in the art. As a non-limiting example, spleen cells and myeloma cells can be pelleted together. The pellet can then be slowly re-suspended, over thirty seconds, in 1 mL of 50% (w/v) PEG/PBS solution (PEG molecular weight 1,450, Sigma) at 37° C. The fusion can then be stopped by slowly adding 10.5 mL of RPMI 1640 medium containing 25 mM Hepes (37° C.) over one minute. The fused cells are centrifuged for five minutes at 500 to 1500 rpm. The cells are then re-suspended in HAT medium (RPMI 1640 medium containing 25 mM Hepes, 10% Fetal Clone I serum (Hyclone), 1 mM sodium pyruvate, 4 mM L-glutamine, 10 μg/mL gentamicin, 2.5% Origen culturing supplement (Fisher), 10% 653-conditioned RPMI 1640/Hepes media, 50 μM 2-mercaptoethanol, 100 μM hypoxanthine, 0.4 μM aminopterin, and 16 μM thymidine) and then plated at 200 μL/well in fifteen 96-well flat bottom tissue culture plates. The plates are then placed in a humidified 37° C. incubator containing 5% $CO_2$ and 95% air for seven to ten days.

Detection of Human IgG Anti-Dengue virus Antibodies in Mouse Serum

Solid phase EIA's can be used to screen mouse sera for human IgG antibodies specific for human Dengue virus. Briefly, plates can be coated with Dengue virus at 2 μg/mL in PBS overnight. After washing in 0.15M saline containing 0.02% (v/v) Tween 20, the wells can be blocked with 1% (w/v) BSA in PBS, 200 μL/well for one hour at room temperature. Plates are used immediately or frozen at −20° C. for future use. Mouse serum dilutions are incubated on the Dengue virus coated plates at 50 μL/well at room temperature for one hour. The plates are washed and then probed with 50 μL/well HRP-labeled goat 25 anti-human IgG, Fc specific diluted 1:30,000 in 1% BSA-PBS for one hour at room temperature. The plates can again be washed and 100 μL/well of the citrate-phosphate substrate solution (0.1M citric acid and 0.2M sodium phosphate, 0.01% $H_2O_2$ and 1 mg/mL OPD) is added for fifteen minutes at room temperature. Stop solution (4N sulfuric acid) is then added at 25 μL/well and the OD's are read at 490 nm via an automated plate spectrophotometer.

Detection of Completely Human Immunoglobulins in Hybridoma Supernates

Growth positive hybridomas secreting fully human immunoglobulins can be detected using a suitable EIA. Briefly, 96 well pop-out plates (VWR, 610744) can be coated with 10 μg/mL goat anti-human IgG Fc in sodium carbonate buffer overnight at 4° C. The plates are washed and blocked with 1% BSA-PBS for one hour at 37° C. and used immediately or frozen at −20° C. Undiluted hybridoma supernatants are incubated on the plates for one hour at 37° C. The plates are washed and probed with HRP labeled goat anti-human kappa diluted 1:10,000 in 1% BSA-PBS for one hour at 37° C. The plates are then incubated with substrate solution as described above.

Determination of Fully Human Anti-Dengue Virus Reactivity

Hybridomas, as above, can be simultaneously assayed for reactivity to Dengue virus using a suitable RIA or other assay. For example, supernatants are incubated on goat anti-human IgG Fc plates as above, washed and then probed with radiolabeled Dengue virus with appropriate counts per well for one hour at room temperature. The wells are washed twice with PBS and bound radiolabeled Dengue virus is quantitated using a suitable counter.

Human anti-Dengue virus secreting hybridomas can be expanded in cell culture and serially subcloned by limiting dilution. The resulting clonal populations can be expanded and cryopreserved in freezing medium (95% FBS, 5% DMSO) and stored in liquid nitrogen.

Isotyping

Isotype determination of the antibodies can be accomplished using an EIA in a format similar to that used to screen the mouse immune sera for specific titers. Dengue virus can be coated on 96-well plates as described above and purified antibody at 2 μg/mL can be incubated on the plate for one hour at room temperature. The plate is washed and probed with HRP labeled goat anti-human $IgG_1$ or HRP labeled goat anti-human $IgG_3$ diluted at 1:4000 in 1% BSA-PBS for one hour at room temperature. The plate is again washed and incubated with substrate solution as described above.

Binding Kinetics of Human Anti-Dengue Virus Antibodies with Dengue Virus

Binding characteristics for antibodies can be suitably assessed using an Dengue virus capture EIA and BIAcore technology, for example. Graded concentrations of purified human Dengue virus antibodies can be assessed for binding to EIA plates coated with 2 μg/mL of Dengue virus in assays as described above. The OD's can be then presented as semi-log plots showing relative binding efficiencies.

Quantitative binding constants can be obtained, e.g., as follows, or by any other known suitable method. A BIAcore CM-5 (carboxymethyl) chip is placed in a BIAcore 2000 unit. HBS buffer (0.01 M HEPES, 0.15 M NaCl, 3 mM EDTA, 0.005% v/v P20 surfactant, pH 7.4) is flowed over a flow cell of the chip at 5 μL/minute until a stable baseline is obtained. A solution (100 μL) of 15 mg of EDC (N-ethyl-N'-(3-dimethyl-aminopropyl)-carbodiimide hydrochloride) in 200 μL water is added to 100 μL of a solution of 2.3 mg of NHS(N-hydroxysuccinimide) in 200 μL water. Forty (40) μL of the resulting solution is injected onto the chip. Six (6) μL of a solution of human Dengue virus (15 μg/mL in 10 mM sodium acetate, pH 4.8) is injected onto the chip, resulting in an increase of ca. 500 RU. The buffer is changed to TBS/Ca/Mg/BSA running buffer (20 mM Tris, 0.15 M sodium chloride, 2 mM calcium chloride, 2 mM magnesium acetate, 0.5% Triton X-100, 25 µg/mL BSA, pH 7.4) and flowed over the chip overnight to equilibrate it and to hydrolyze or cap any unreacted succinimide esters.

Antibodies are dissolved in the running buffer at 33.33, 16.67, 8.33, and 4.17 nM. The flow rate is adjusted to 30 µL/min and the instrument temperature to 25° C. Two flow cells are used for the kinetic runs, one on which Dengue virus had been immobilized (sample) and a second, underivatized flow cell (blank). 120 µL of each antibody concentration is injected over the flow cells at 30 µL/min (association phase) followed by an uninterrupted 360 seconds of buffer flow (dissociation phase). The surface of the chip is regenerated (tissue necrosis factor alpha/antibody complex dissociated) by two sequential injections of 30 µL each of 2 M guanidine thiocyanate.

Analysis of the data is done using BIA evaluation 3.0 or CLAMP 2.0, as known in the art. For each antibody concentration the blank sensogram is subtracted from the sample sensogram. A global fit is done for both dissociation ($k_d$, $sec^{-1}$) and association ($k_a$, $mol^{-1}$ $sec^{-1}$) and the dissociation constant ($K_D$, mol) calculated ($k_d/k_a$). Where the antibody affinity is high enough that the RUs of antibody captured are >100, additional dilutions of the antibody are run.

Results and Discussion

Generation of Anti-Human Dengue Virus Monoclonal Antibodies

Several fusions are performed and each fusion is seeded in fifteen plates (1440 wells/fusion) that yield several dozen antibodies specific for Dengue virus or Dengue virus-infected cells. Of these, some are found to consist of a combination of human and mouse Ig chains. The remaining hybridomas secrete anti-Dengue virus antibodies consisting solely of human heavy and light chains.

Binding Kinetics of Human Anti-Dengue Virus Antibodies

ELISA analysis confirms that purified antibody from most or all of these hybridomas bind Dengue virus in a concentration-dependent manner. In this case, the avidity of the antibody for its cognate antigen (epitope) is measured. It should be noted that binding Dengue virus proteins directly to the EIA plate can cause denaturation of the protein and the apparent binding affinities cannot be reflective of binding to undenatured protein. Fifty percent binding is found over a range of concentrations.

Quantitative binding constants are obtained using BIAcore analysis of the human antibodies and reveals that several of the human monoclonal antibodies are very high affinity with $K_D$ in the range of $1 \times 10^{-9}$ to $7 \times 10^{-12}$. See FIG. 1, Panels A, B and C.

Conclusions

Several fusions are performed utilizing splenocytes from hybrid mice containing human variable and constant region antibody transgenes that are immunized with human Dengue virus. A set of several completely human Dengue virus reactive IgG monoclonal antibodies of the IgG1 isotype are generated. The completely human anti-Dengue virus antibodies are further characterized. Several of generated antibodies have affinity constants between $1 \times 10^9$ and $9 \times 10^{12}$. The relatively high affinities of these fully human monoclonal antibodies make them suitable for therapeutic applications in Dengue virus-dependent diseases, pathologies or related conditions.

EXAMPLE 3

Isolation of Antibody by Phage Display of Human Immune Repertoire Reactive to Dengue Virus The generation of antibodies from immune individuals as carried out in this invention essentially involves four stages: (1) preparation of RNA from a source of antibody-producing cells, (2) reverse transcription and PCR amplification of heavy (Fd part) and light chains, (3) cloning of PCR inserts into a phagemid vector (pComb3) and expression of a Fab library on the surface of phage, (4) panning of the library against antigen to select specific Fabs. The antibodies selected will depend primarily on the RNA source, PCR amplification and the antigen used for panning.

Dengue Fab Antibody Isolation

Phage Library and Antibodies

Antibody phage-display libraries were prepared from RNA isolated from human PBMC from a donor who recovered from infection with Dengue virus. The ability of serum obtained from the donor to neutralize Dengue virus in vitro is shown in Table 1.

TABLE 1

| | Serum Dengue Virus Neutralization Titer Dengue Virus Serotype | | | |
|---|---|---|---|---|
| Sample | 1 | 2 | 3 | 4 |
| 1 | 3980 | 1070 | 87 | 170 |
| 2 | 300 | 170 | 220 | 20 |

The resulting library was panned for four consecutive rounds of selection with increasing washing stringency. After the final round of panning, colonies were picked, expanded, and phage isolated. Specific binders were identified in phage ELISA. Soluble Fab antibody was prepared by digestion of isolated phagemid DNA which was digested to remove the cpIII gene, re-ligated, and used to transform E. coli.

Specifically, peripheral blood mononuclear cells (PBMC) were isolated from blood of a human patient who had survived a Dengue infection. The blood serum was lysed by vigorous mixing with denaturant solution and RNA was prepared by adding 2 M sodium acetate (pH 4.0) lysate. The samples were extracted with acidic phenol (saturated with 0.1 M citrate buffer [pH 4.3] [Sigma]) and a chloroformisoamyl alcohol mixture (24:1). After being incubated on ice for 15 minutes, the samples were centrifuged at 10,000×g for 20 minutes at 4° C. RNA was precipitated from the supernatant by the addition of 40 µg of glycogen (Boehringer Mannheim, Indianapolis, Ind.) and 15 ml of 2-propanol (Sigma), overnight incubation at −20° C., and centrifugation at 10,000×g for 20 minutes at 4° C. The RNA pellet was re-dissolved in 3 ml of denaturant solution and re-precipitated for 3 hours at −20° C. after the addition of an equal volume of 2-propanol. RNA was pelleted in a microcentrifuge, washed twice with 70% ethanol, and re-suspended in diethylpyrocarbonate-treated water.

Library Construction

First-strand cDNA was prepared by priming with oligo d(T) with a cDNA kit (Boehringer Mannheim) as recommended by the manufacturer. The IgG1 Fd region and whole kappa and lambda light chains were then amplified by PCR. Phage display libraries were constructed in the phage display vector pComb3H. Briefly, the light-chain and heavy-chain PCR fragments were cloned into the SacI-XbaI and XhoI-SpeI restriction sites of the phagemid, respectively. Ligation products were ethanol precipitated and electroporated into *Escherichia coli* XLI-Blue cells (Stratagene, La Jolla, Calif.). The transformed *E. coli* cultures were grown in SOC medium and then in SB medium containing 10 μg of tetracycline per ml and 20 μg of carbenicillin per ml, each for 1 hour at 37° C. The carbenicillin concentration was increased to 50 μg/ml, and after the cells had grown for 1 hour, phage particle assembly was initiated by the addition of VCS-M13 helper phage ($5\times10^{11}$ PFU). After an additional 2 hours of culture, kanamycin was added to a concentration of 50 μg/ml and the culture was grown overnight at 30° C. Phage was recovered from the cultures by removing bacteria by centrifugation at 4,000×g and precipitating phage from the supernatant by addition of 4% polyethylene glycol and 0.5 M NaCl and incubation of the mixture on ice for 30 minutes. After centrifugation, phage pellets were re-suspended in 500 μl of phosphate-buffered saline (PBS-4% nonfat dry milk (Bio-Rad, Hercules, Calif.) and centrifuged for 5 minutes in a microcentrifuge to pellet bacterial debris.

Affinity Selection of Ab Libraries on Dengue Antigens

The Dengue antigens used for selection (panning) were NS1 proteins obtained from a virus infected cell lysate.

A microtiter plate (Costar, Cambridge, Mass.) was coated overnight at 4° C. with Dengue virus antigens. The plates were washed and blocked with 4% nonfat dry milk (Bio-Rad) for 1 hour at 37° C. The milk solution was shaken out, phage solution was added to each well, and the mixture was incubated for 2 hours at 37° C. on a rocker platform. The phage solution was removed, and the wells were washed. Bound phage was eluted with glycine buffer (pH 2.2) and neutralized with 2 M Tris base. Eluted phage was re-amplified for the next round of panning. The libraries were panned for four or five consecutive rounds with increasing washing stringency (2, 5, and 10 wash steps thereafter, each consisting of a 5 minute incubation and vigorous pipetting). Phagemid DNA, isolated after the last round of panning, was digested with NheI and SpeI restriction endonucleases and re-ligated to excise the cpIII gene and obtain plasmids producing soluble Fabs.

Screening of Soluble Fab Fragments

Microtiter wells were coated overnight at 4° C. with the two Dengue antigens used for panning and a control antigen, ovalbumin (4 μg/ml) (Pierce, Rockford, Ill.). Soluble Fabs were tested by an enzyme-linked immunosorbent assay (ELISA). One of these Fabs was designated Sid33, and was shown to bind to Dengue virus NS 1 protein.

DNA Sequencing

Fabs were analyzed for their DNA sequence with a 373A or 377A automated DNA sequencer (ABI, Foster City, Calif.), using a Taq fluorescent dideoxy terminator cycle-sequencing kit (ABI).

EXAMPLE 4

Generation of Human IgG Monoclonal Antibodies Reactive to Dengue Virus

Expression and Purification of Antibody

The recombinant antibody DEN3, which is an IgG molecule, was expressed in the vector pDR12. The vector contains a light chain and heavy chain expression cassette in which transcription is driven from a human cytomegalovirus promoter. The heavy chain expression cassette contains the genomic human IgG1 gene. Selection and amplification of the plasmid was done on the basis of expression of the gene for glutamine synthetase. (See Bebbington et al., "High-level Expression of a Recombinant Antibody from Myeloma Cells Using a Glutamine Synthetase Gene as an Amplifiable Selectable Marker", 10 BIO/TECHNOLOGY, 169-275 (1992)).

DNA encoding the Fab Sid33 was cloned into the pDR12 expression vector to produce pDRSid33, which places the Fab encoding sequences in the framework of an IgG1 antibody molecule. The full IgG antibody molecule that binds to Dengue virus NS 1 protein is referred to herein as DEN3. pDRSid33 DNA was cut with Sal1 and transfected into Chinese hamster ovary cells (CHO-K1 cells; American Type Culture Collection, Manassas, Va.) using lipofectin reagent per the manufacturer recommendations (Life Technologies, Grand Island, N.Y.). Cells were distributed in six-well tissue culture treated plates and transfected clones were selected with L-Methionine Sulfoximine ranging in concentration from 40 to 140 μM (Sigma, St. Louis, Mo.). Post-transfection discrete colonies were assayed by enzyme-linked immunosorbent assay (ELISA) for antibody production. The highest producers were cloned by limiting dilution, expanded and grown in three-liter spinner flasks.

The recombinant DEN3 IgG1 monoclonal antibody was expressed in CHO-K1 cells in glutamine-free Glasgow minimum essential medium (GMEM, Sigma, St. Louis, Mo.) supplemented with 10% dialyzed fetal calf serum (FCS, Tissue Culture Biologicals, Tulare, Calif.), MEM non-essential amino acids (Gibco-BRL, Grand Island, N.Y.), 1 mM MEM sodium pryuvate (Gibco-BRL), 500 μM L-glutamic acid, 500 μM L-asparagine, 30 μM adenosine, 30 μM adenosine, 30 μM guanosine, 30 μM cytidine, 30 μM uridine, 10 μM thymidine (Sigma), 100 U of penicillin/mL 100 μg of streptomycin/mL, and 50 methonine sulfoximine (Sigma) in a 3 liter spinner flask. The supernatant was sterile filtered and purified over protein A-Sepharose Fast Flow (Pharmacia, Arlington Heights, Ill.). The antibody was eluted in 0.1 M citric acid, pH 3.0. The pH of the antibody solution was immediately brought to neutrality by the addition of 1 M Tris (pH 9.0), and the antibody was dialyzed against phosphate-buffered saline (PBS). Antibody concentrations were determined by absorbance at 280 nm and confirmed by sodium dodecyl sulfate-polyacrylamide gel electrophoresis (SDS-PAGE). Antibody yields using this method ranged from 3 to 18 mg/Liter.

In anticipation of animal experiments care was taken to minimize contamination with endotoxin, which was monitored using a quantitative chromagenic Limulus Amoebecyte Lysate assay (BioWhittaker, Walkersville, Md.) performed according to the manufacturer's recommendations. When detected, endotoxin was removed using polymyxin affinity column chromatography (Bio-Rad, Hercules, Calif.).

EXAMPLE 5

Study Using Anti-Dengue Virus Antibodies and Controls to Prevent or Treat Dengue Virus Infection Clinical Trials Antibodies of the invention or fragments thereof may be tested in in vitro assays and animal models, and may be further evaluated for safety, tolerance, and pharmacokinetics in groups of normal healthy adult volunteers. The volunteers are administered intramuscularly, intravenously or by an alternative delivery system a single dose of 0.5 mg/kg, 3 mg/kg, 5 mg/kg, 10 mg/kg or 15 mg/kg of an antibody or fragment thereof which immunospecifically binds to a Dengue virus NS protein. Each volunteer is monitored at least 24 hours prior to receiving the single dose of the antibody or fragment thereof and each volunteer will be monitored for at least 48 hours after receiving the dose at a clinical site. Then volunteers are monitored as outpatients on days 3, 7, 14, 21, 28, 35, 42, 49, and 56 post-dose.

Blood samples are collected via an indwelling catheter or direct venipuncture using 10 ml Vacutainer tubes at the following intervals: (1) prior to administering the dose of the antibody or antibody fragment; (2) during the administration of the dose of the antibody or antibody fragment; (3) 5 minutes, 10 minutes, 15 minutes, 20 minutes, 30 minutes, 1 hour, 2 hours, 4 hours, 8 hours, 12 hours, 24 hours, and 48 hours after administering the dose of the antibody or antibody fragment; and (4) 3 days, 7 days 14 days, 21 days, 28 days, 35 days, 42 days, 49 days, and 56 days after administering the dose of the antibody or antibody fragment. Samples are allowed to clot at room temperature and serum will be collected after centrifugation.

The antibody or antibody fragment is partially purified from the serum samples and the amount of antibody or antibody fragment in the samples will be quantitated by ELISA. Briefly, the ELISA consists of coating microtiter plates overnight at 4° C. with an antibody that recognizes the antibody or antibody fragment administered to the volunteer. The plates are then blocked for approximately 30 minutes at room temperate with PBS-Tween-0.5% BSA. Standard curves are constructed using purified antibody or antibody fragment, not administered to a volunteer. Samples are diluted in PBS-Tween-BSA. The samples and standards are incubated for approximately 1 hour at room temperature. Next, the bound antibody is treated with a labeled antibody (e.g., horseradish peroxidase conjugated goat-anti-human IgG) for approximately 1 hour at room temperature. Binding of the labeled antibody is detected, e.g., by a spectrophotometer.

The concentration of antibody or antibody fragment levels in the serum of volunteers are corrected by subtracting the predose serum level (background level) from the serum levels at each collection interval after administration of the dose. For each volunteer the pharmacokinetic parameters are computed according to the model-independent approach (Gibaldi et al. (Eds.), *Pharmacokinetics, 2nd Supplementary Edition*, (Marcel Dekker, New York (1982)) from the corrected serum antibody or antibody fragment concentrations.

Treatment of Dengue Virus Infection in Humans Using an Anti-Dengue Virus NS Protein Antibody The anti-Dengue Virus NS Protein antibody DEN3 may be used to treat patients infected with Dengue virus. Patients with the symptoms of a Dengue virus infection will receive a single dose of either 0.1, 1.0, 5.0 or 10 milligrams of DEN3 per kilogram bodyweight. Another group of patients will receive standard treatment for Dengue virus infection. The DEN3 is administered as a single, intravenous infusion over a 60 minute period. Clinical assessment, vital signs, and laboratory parameters are measured before, during and periodically for 28 days after the infusion. Accordingly, human treatment of Dengue virus infection in human patients using DEN3 is expected to provide a suitable treatment, including the reduction of severity of symptoms and duration of disease, as described herein.

Equivalents

Those skilled in the art will recognize, or be able to ascertain using no more than routine experimentation, many equivalents to the specific embodiments of the invention described herein. Such equivalents are intended to be encompassed by the following claims.

REFERENCES

1. C. M. Rice, "Flaviviridae: The Viruses and Their Replication", *Fields Virology, 3rd Edition*, (Fields et al. (Eds.), Lippincott-Raven, Philadelphia, Pa. (1996)), 931-959.
2. Wang et al., "Evolutionary Relationships of Endemic/Epidemic and Sylvatic Dengue Viruses", 74 J. Virol., 3227-3234 (2000).
3. R. Rico-Hesse, "Molecular Evolution and Distribution of Dengue Viruses Type 1 and 2 in Nature", 174 Virology, 479-493 (1990).
4. B. L. Innis, "Antibody Responses to Dengue Virus Infection", *Dengue and Dengue Hemorrhagic Fever*, (D. J. Gubler and G. Kuno (Eds.), CAB International, Cambridge (1997)) 221-243.
5. Innis et al., "An Enzyme-Linked Immunosorbent Assay to Characterize Dengue Infections Where Dengue and Japanese Encephalitis Co-Circulate", 40 Am. J. Trop. Med. Hyg., 418-427 (1989).
6. A. B. Sabin, "Research on Dengue During World War II", 1 Am. J. Trop. Med. Hyg., 30-50 (1952).
7. R. M. Myers and M. J. Varkey, "A Note on Sequential Dengue Infection, Presumptive and Proved, with Report of an Instance of a Third Proved Attack in One Individual", 59 Indian J. Med. Res., 1231-1236 (1971).
8. Halstead et al., "Observations Related to Pathogenesis of Dengue Hemorrhagic Fever. IV: Relation of Disease Severity to Antibody Response and Virus Recovered", 42 Yale J. Biol. Med., 311-328 (1970).
9. Kliks et al., "Evidence that Maternal Dengue Antibodies are Important in the Development of Dengue Hemorrhagic in Infants", 38 Am. J. Trop. Med. hyg., 411-419 (1988).
10. Halstead et al., "Infant Dengue Hemorrahagic Fever: Research Opportunities Ignored", Emerg. Infect. Dis. (submitted 2002).
11. S. B. Halstead, "Immunological Parameters of Togavirus Disease Syndromes", *The Togaviruses, Biology Structure, Replication*, (R. W. Schlesinger (Ed.), Academic Press, New York, N.Y. (1980)) 107-173.
12. S. B. Halstead, "Immune Enhancement of Viral Infection", 31 Prog. Allergy, 301-364 (1982).
13. S. B. Halstead, "In Vivo Enhancement of Dengue Virus Infection in Rhesus Monkeys by Passively Transferred Antibody", 140 J. Infect. Dis., 527-533 (1979).
14. Winter et al., "An Insular Outbreak of Dengue Hemorrhagic Fever. I: Epidemiologic Observations", 17 Am. J. Trop. Med. Hyg., 590-599 (1968).
15. Burke et al., "A Prospective Study of Dengue Infections in Bangkok", 38 Am. J. Trop. Med. Hyg., 172-180 (1988).
16. Graham et al., "A Prospective Seroepidemiologic Study on Dengue in Children Four to Nine Years of age in Yogyakarta, Indonesia. I: Studies in 1995-1996", 61 Am. J. Trop. Med. Hyg., 412-9 (1999).
17. Sangkawibha et al., "Risk Factors in Dengue Shock Syndrome: A Prospective Epidemiologic Study in Rayong, Thailand. I: The 1980 Outbreak", 120 Am. J. Epidemiol., 653-669 (1984).
18. Halstead et al., "Studies on the Pathogenesis of Dengue Infection in Monkeys. II: Clinical Laboratory Responses to Heterologous Infection", 128 J. Infect. Dis., 15-22 (1973).
19. Vaughn et al., "Dengue Viremia Titer, Antibody Response Pattern, and Virus Serotype Correlate with Disease Severity", 181 J. Infect. Dis., 2-9 (2000).

20. Halstead et al., "Heterogeneity of Infection Enhancement of Dengue 2 Strains by Monoclonal Antibodies", 132 J. IMMUNOL., 1529-1532 (1984).
21. Halstead et al., "In Vitro Virulence Marker: Growth of Dengue-2 Virus in Human Leukocyte Suspension Cultures", 31 INFECT. IMMUN., 102 (1981).
22. D. M. Morens and S. B. Halstead, "Disease Severity-Related Antigenic Differences in Dengue 2 Strains Detected by Dengue 4 Monoclonal Antibodies", 22 J MED VIROL., 169-174 (1987).
23. D. M. Morens and S. B Halstead, "Measurement of Antibody-Dependent Infection Enhancement of Four Dengue Virus Serotypes by Monoclonal and Polyclonal Antibodies", 71 J. GEN. VIROL., 2909-2914 (1990).
24. Kliks et al., "Antibody-Dependent Enhancement of Dengue Virus Growth in Human Monocytes as a Risk Factor for Dengue Hemorrhagic Fever", 40 AM. J. TROP. FILED HYG., 444-451 (1989).
25. Watts et al., "Failure of Secondary Infection with American Genotype Dengue 2 to Cause Dengue Haemorrhagic Fever", [see comments], 354 LANCET, 1431-4 (1999).
26. Kochel et al., "Neutralization of American Genotype Dengue 2 Viral Infection by Dengue 1 Antibodies May Have Prevented Dengue Hemorrhagic Fever in Iquitos, Peru", LANCET [in press 2002].
27. Guzman et al., "Do Escape Mutants Explain Rapid Increases in Dengue Case-Fatality Rates within Epidemics?", 355 LANCET, 1902-3 (2000).
28. S. B. Halstead and S. B. Russ, "Subclinical Japanese Encephalitis. II: Antibody Responses of Americans to Single exposure to JE Virus", 75 AM. J. HYG., 202-211 (1962).
29. Guzman et al., "Enhanced Severity of Secondary Dengue 2 Infections Occurring at an Interval of 20 Compared with 4 Years After Dengue 1 Infection", PANAMERICAN JOURNAL OF EPIDEMIOLOGY in press (2002).

What is claimed is:

1. An isolated mammalian anti-Dengue virus antibody, comprising at least one variable region comprising the amino acid sequence set forth in SEQ ID NO: 4.

2. An antibody according to claim 1, wherein said antibody binds Dengue virus NS-1 protein.

3. A composition comprising at least one isolated mammalian anti-Dengue virus antibody having at least one variable region comprising the amino acid sequence set forth in SEQ ID NO: 4, and at least one pharmaceutically acceptable carrier or diluent.

4. An isolated mammalian anti-Dengue virus antibody having at least one variable region comprising SEQ ID NO: 4 produced by a method comprising providing a host cell or a non-human transgenic animal or transgenic plant or plant cell capable of expressing in recoverable amounts said antibody.

5. A medical device, comprising at least one isolated mammalian anti-Dengue virus antibody having at least one variable region comprising SEQ IN NO: 4, wherein said device is suitable to contacting or administering said at least one anti-Dengue virus antibody by at least one mode selected from the group consisting of parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

* * * * *